US012569342B2

(12) United States Patent
Skarsgard

(10) Patent No.: US 12,569,342 B2
(45) Date of Patent: Mar. 10, 2026

(54) APPARATUS AND METHODS FOR CLAMPING A MITRAL VALVE

(71) Applicant: Vesalius Cardiovascular Inc., Vancouver (CA)

(72) Inventor: Peter Lloyd Skarsgard, Vancouver (CA)

(73) Assignee: VESALIUS CARDIOVASCULAR INC., Vancouver (CA)

( * ) Notice: Subject to any disclaimer, the term of this patent is extended or adjusted under 35 U.S.C. 154(b) by 926 days.

(21) Appl. No.: 17/789,601

(22) PCT Filed: Mar. 5, 2021

(86) PCT No.: PCT/CA2021/050296
    § 371 (c)(1),
    (2) Date: Jun. 28, 2022

(87) PCT Pub. No.: WO2021/179065
    PCT Pub. Date: Sep. 16, 2021

(65) Prior Publication Data
    US 2023/0029712 A1     Feb. 2, 2023

Related U.S. Application Data

(60) Provisional application No. 62/987,240, filed on Mar. 9, 2020.

(51) Int. Cl.
    *A61F 2/24*          (2006.01)
(52) U.S. Cl.
    CPC .......... *A61F 2/2454* (2013.01); *A61F 2/2466* (2013.01); *A61F 2220/0008* (2013.01);
    (Continued)

(58) Field of Classification Search
    CPC .... A61F 2/2445; A61F 2/2448; A61F 2/2409; A61F 2/2475; A61F 2/2476
    See application file for complete search history.

(56) References Cited

U.S. PATENT DOCUMENTS 5,776,188 A * 7/1998 Shepherd .............. A61F 2/2409
                                                        623/2.38
6,419,696 B1   7/2002 Ortiz et al.
               (Continued)

FOREIGN PATENT DOCUMENTS

WO      2003020179 A1    3/2003
WO      2007136783 A2   11/2007
               (Continued)

*Primary Examiner* — Alvin J Stewart
(74) *Attorney, Agent, or Firm* — Oyen Wiggs Green & Mutala LLP

(57)                    ABSTRACT

An apparatus for repairing or replacing a mitral valve and a method of using same are disclosed. The apparatus has an atrial band securable to a ring-shaped ventricular band. The ventricular band has an anterior band and a posterior band connectable to the anterior band. The atrial and anterior bands each have a pair of apertures. Each of the apertures is positioned proximate to a respective terminal end of the bands. The apertures of the atrial and anterior bands are arranged to align with one another when their inner surfaces engage. Means are provided to secure the atrial band to the anterior band. When delivered and implanted, the apparatus is arranged to extend across the commissures of the heart, with atrial and anterior bands arranged to press against the atrial and ventricular surfaces of the mitral valve leaflets respectively.

20 Claims, 26 Drawing Sheets

(52) U.S. Cl.
 CPC ................. *A61F 2230/0065* (2013.01); *A61F 2250/0018* (2013.01)

(56) References Cited

U.S. PATENT DOCUMENTS

|            |        |         |                |              |
| ---------- | ------ | ------- | -------------- | ------------ |
| 7,077,861  | B2     | 7/2006  | Spence         |              |
| 7,101,395  | B2     | 9/2006  | Tremulis et al. |             |
| 8,758,372  | B2 *   | 6/2014  | Cartledge ............ | A61B 5/6885 |
|            |        |         |                | 623/2.37     |
| 9,993,339  | B2 *   | 6/2018  | Madjarov ............ | A61F 2/2445 |
| 10,849,751 | B2 *   | 12/2020 | Madjarov ............ | A61F 2/2442 |
| 2002/0173841 | A1   | 11/2002 | Ortiz et al.   |              |
| 2007/0168022 | A1 * | 7/2007  | Eldridge ............... | A61F 2/2409 |
|            |        |         |                | 623/2.4      |
| 2009/0248148 | A1 * | 10/2009 | Shaolian ............... | A61F 2/2442 |
|            |        |         |                | 623/2.37     |
| 2012/0323317 | A1   | 12/2012 | Karapetian et al. |           |
| 2016/0193044 | A1 * | 7/2016  | Achiluzzi ............ | A61F 2/2418 |
|            |        |         |                | 623/2.14     |
| 2016/0346080 | A1 * | 12/2016 | Righini ................ | A61F 2/2412 |
| 2018/0360605 | A1   | 12/2018 | Zerkowski et al. |            |
| 2022/0202570 | A1 * | 6/2022  | Keränen ............... | A61F 2/2448 |
| 2023/0414355 | A1 * | 12/2023 | Conklin ............... | A61F 2/2448 |
| 2025/0235316 | A1 * | 7/2025  | Yellin ................... | A61F 2/2448 |

FOREIGN PATENT DOCUMENTS

|    |               |      |         |              |
| -- | ------------- | ---- | ------- | ------------ |
| WO | 2009094496    | A1   | 7/2009  |              |
| WO | WO-2014144439 | A1 * | 9/2014  | .......... A61F 2/2448 |
| WO | 2015022710    | A1   | 2/2015  |              |
| WO | 2018197721    | A1   | 11/2018 |              |
| WO | 2019081775    | A1   | 5/2019  |              |

* cited by examiner

FIG. 6A
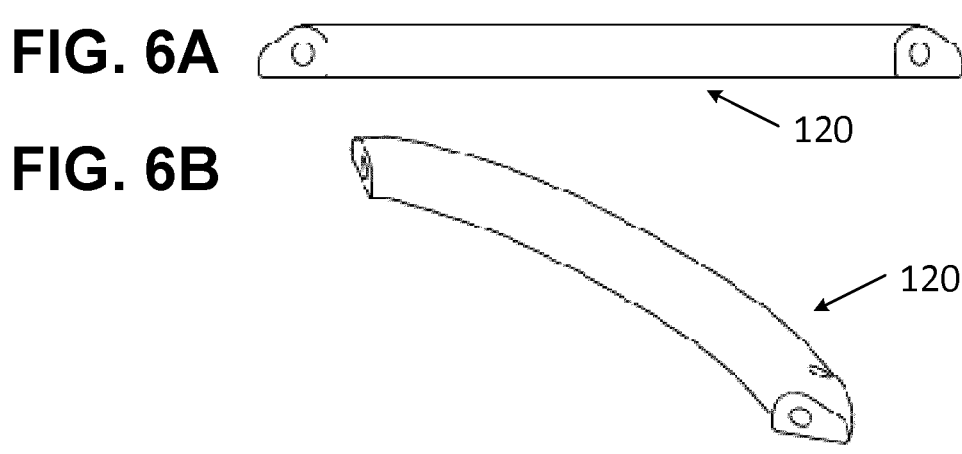
120
FIG. 6B
120
FIG. 6C
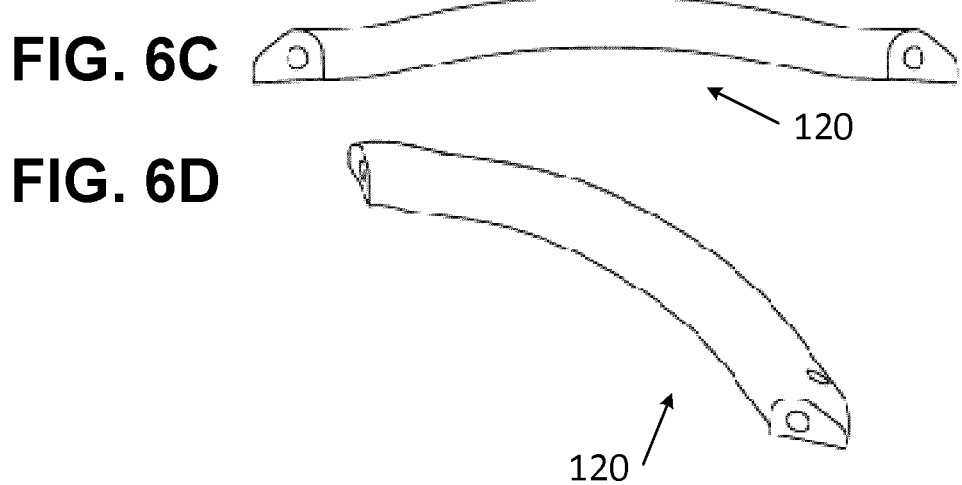
120
FIG. 6D
120
FIG. 6E
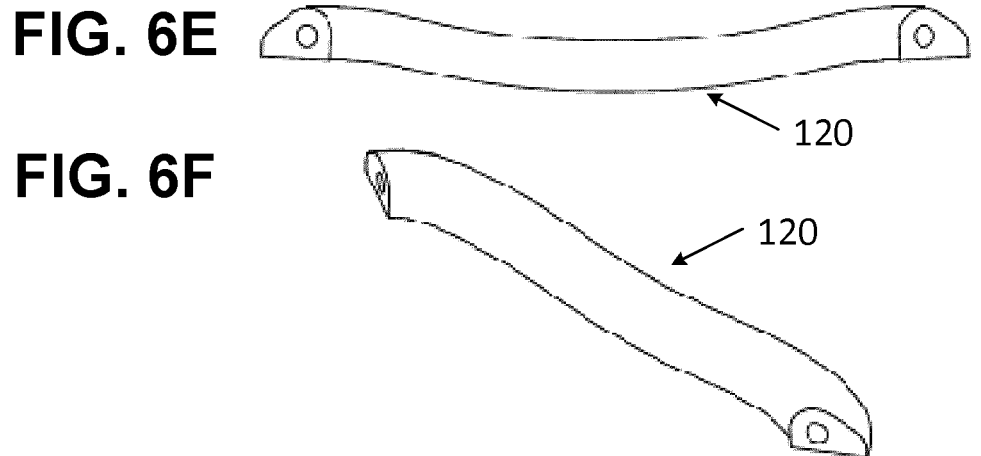
120
FIG. 6F
120

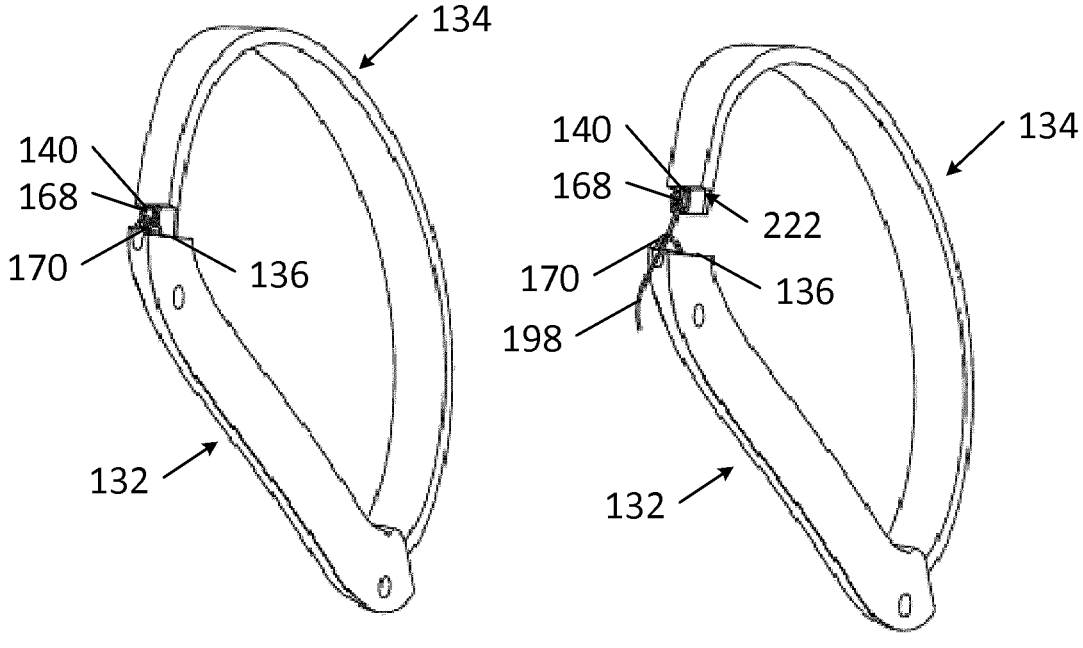
FIG. 7          FIG. 8

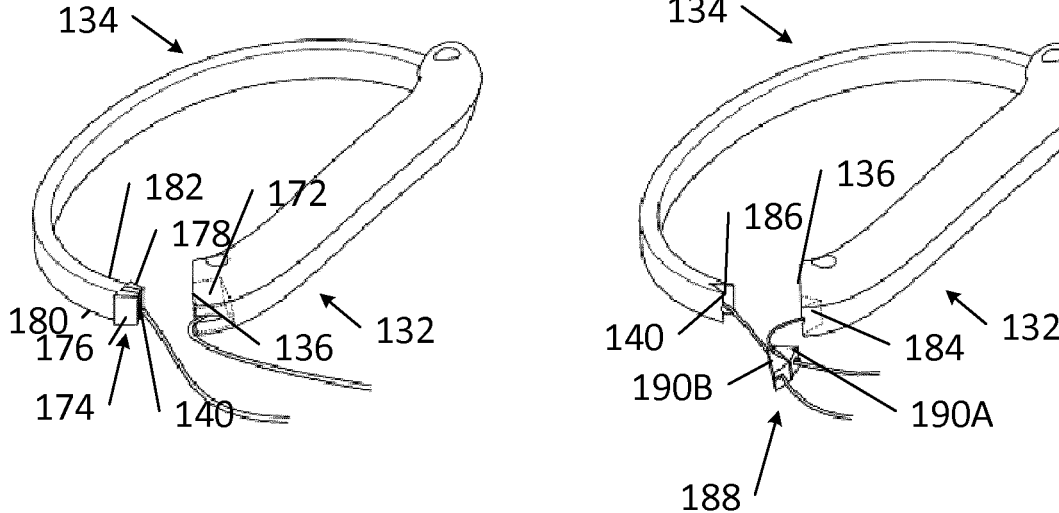
FIG. 9     FIG. 10

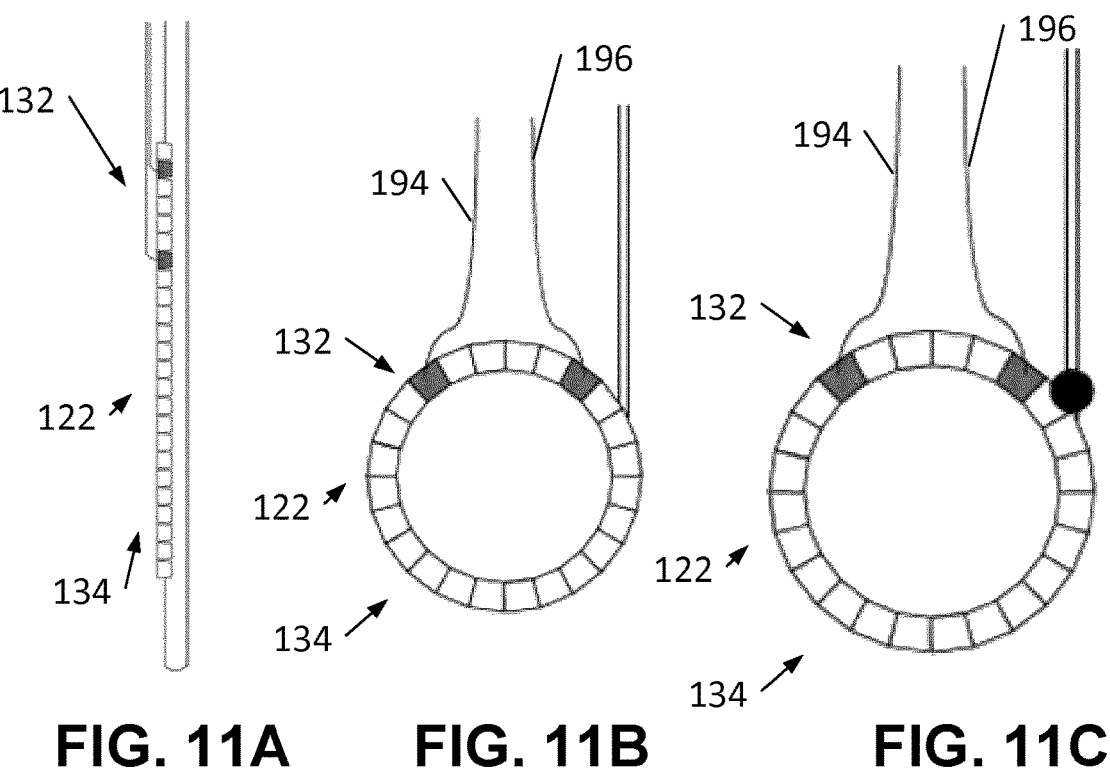
FIG. 11A      FIG. 11B      FIG. 11C
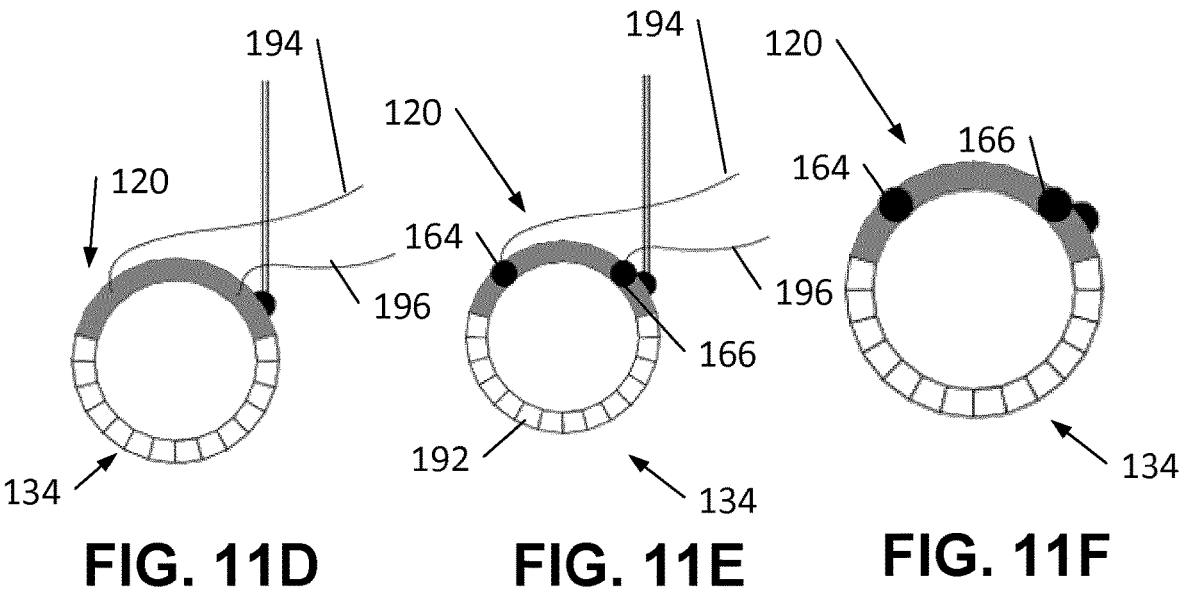
FIG. 11D      FIG. 11E      FIG. 11F

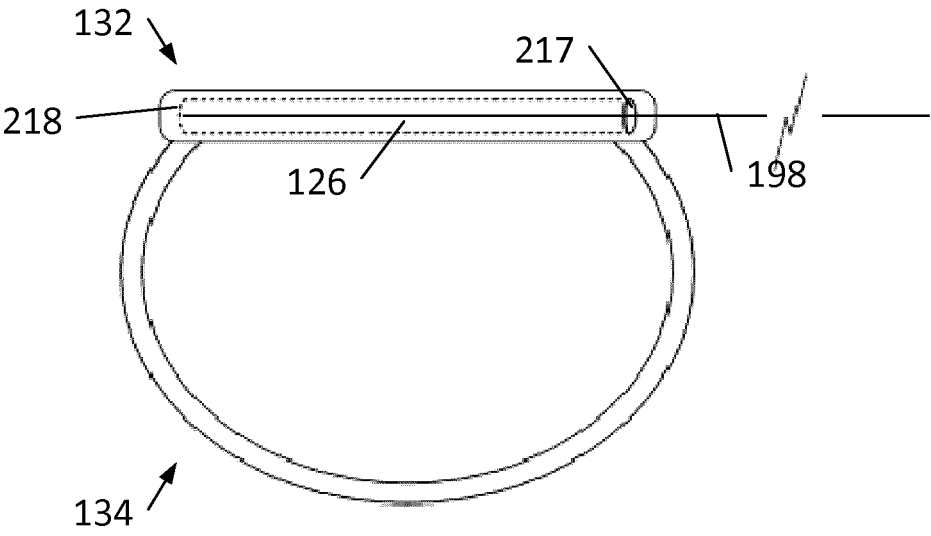
FIG. 19A
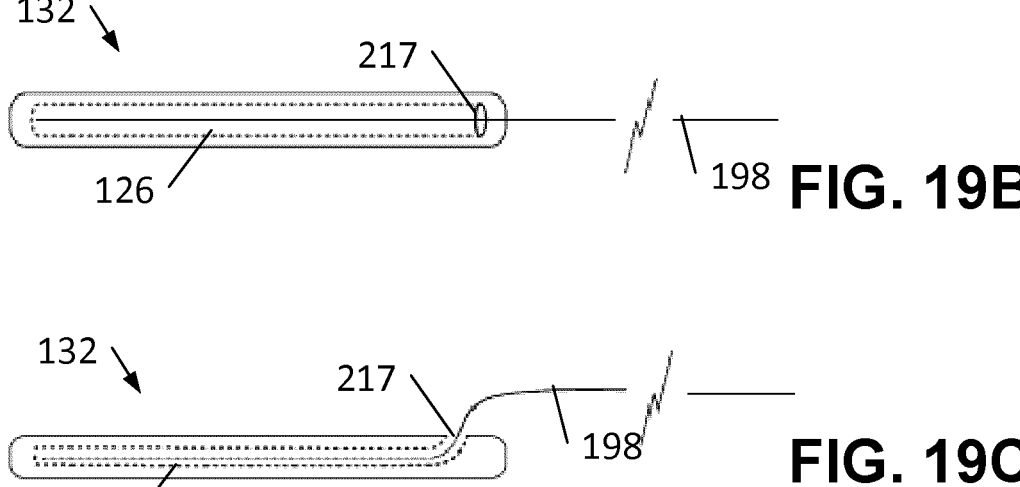
FIG. 19B
FIG. 19C

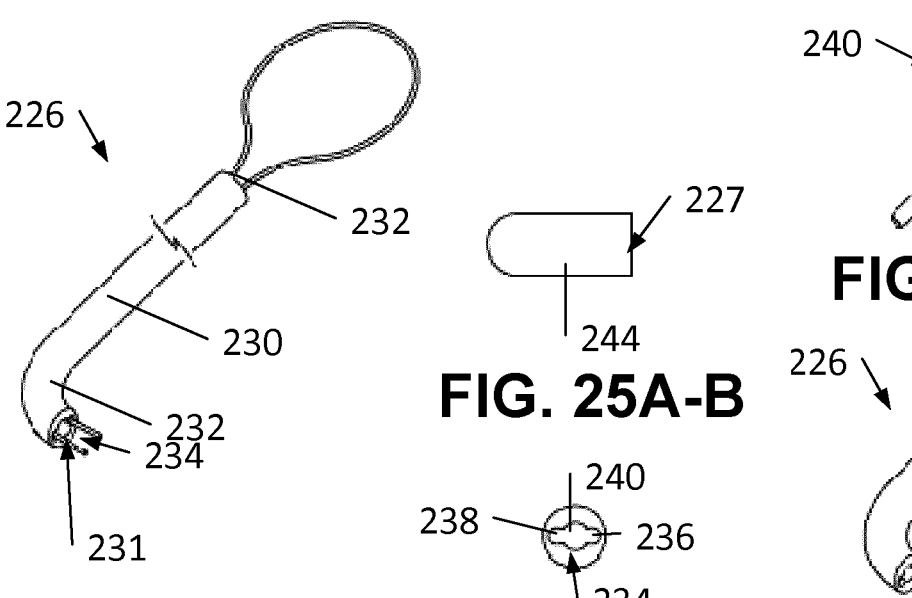
226
232
230
232
234
231
FIG. 25D
227
244
FIG. 25A-B
240
FIG. 25A-B
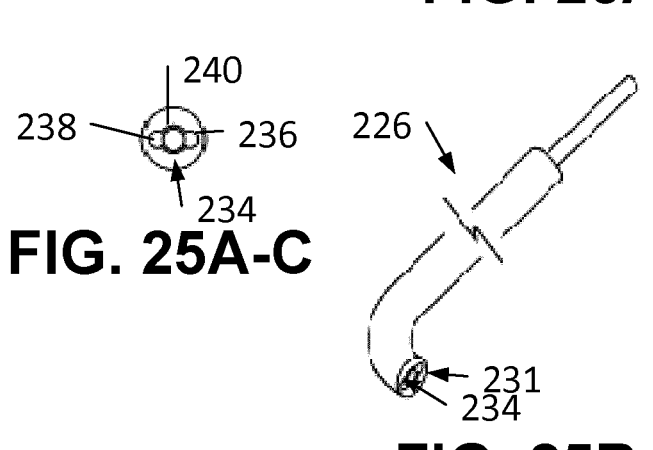
240
238
236
234
FIG. 25A-A
226
231
234
FIG. 25A
226
231
234
FIG. 25E
240
238
236
234
FIG. 25A-C
226
231
234
FIG. 25B
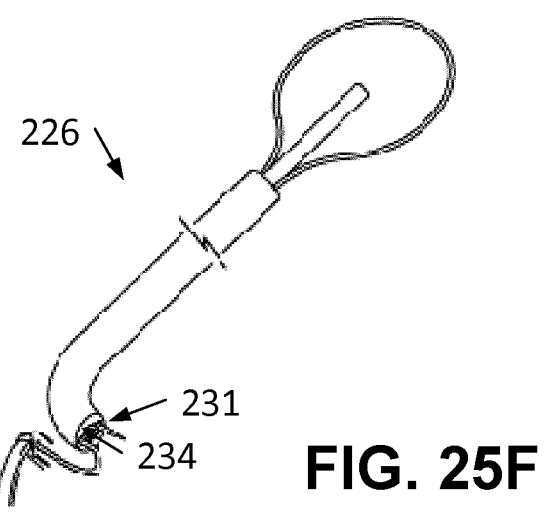
226
231
234
FIG. 25F
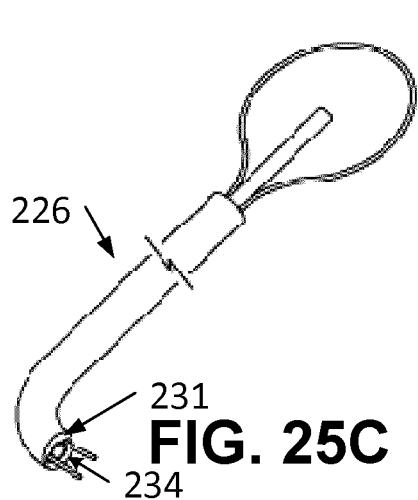
226
231
FIG. 25C
234

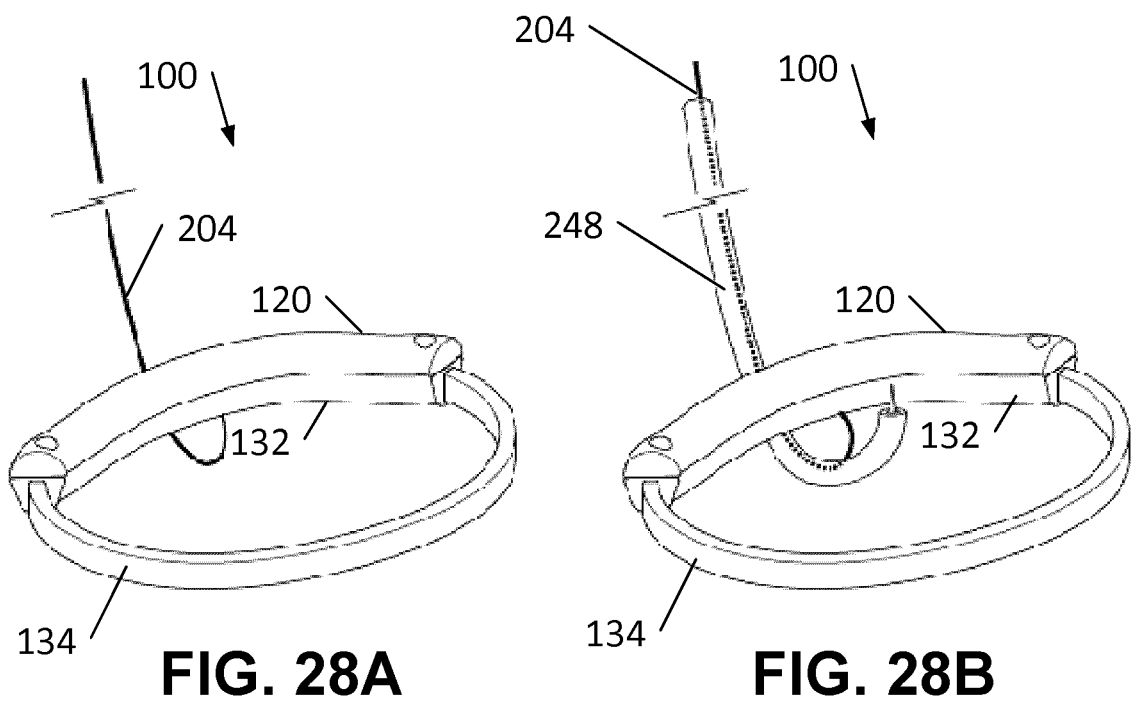
FIG. 28A
FIG. 28B
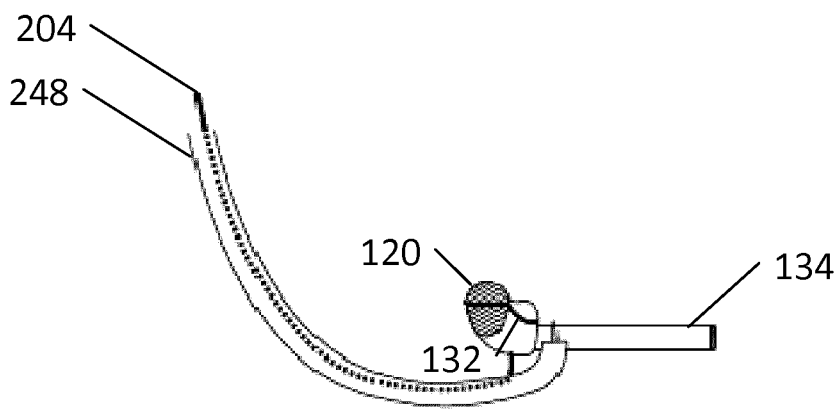
FIG. 28C

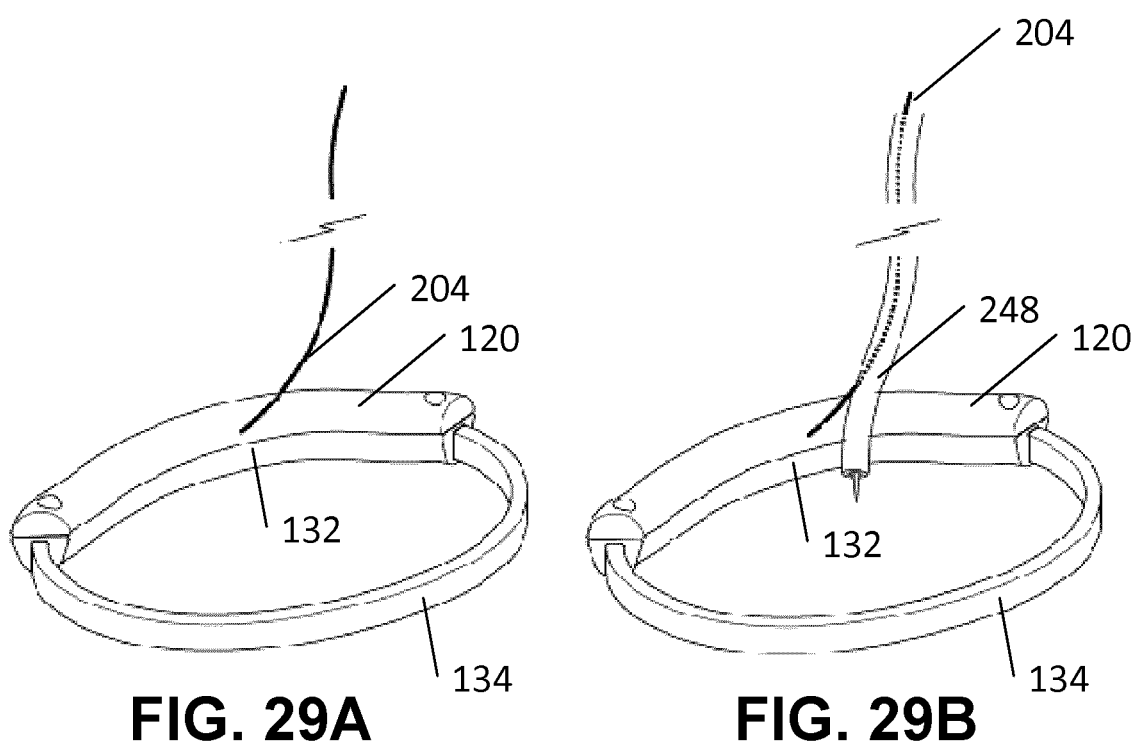
FIG. 29A                    FIG. 29B
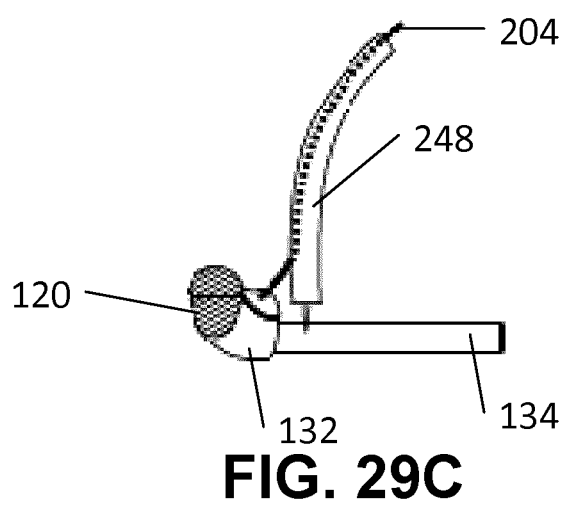
FIG. 29C

APPARATUS AND METHODS FOR CLAMPING A MITRAL VALVE

CROSS-REFERENCE TO RELATED APPLICATION

This application is a 371 national phase entry of Patent Cooperation Treaty application No. PCT/CA2021/050296 filed 5 Mar. 2021, entitled APPARATUS AND METHODS FOR CLAMPING A MITRAL VALVE, which claims priority to, and the benefit of, U.S. provisional patent application No. 62/987,240 filed 9 Mar. 2020. Both of the foregoing applications are hereby incorporated by reference herein in their entireties.

TECHNICAL FIELD

The present invention relates to apparatus for use in repairing or replacing heart valves and methods of use thereof. In particular, the present invention relates to apparatus and methods for clamping a mitral valve.

BACKGROUND

The mitral valve is the most complex of the human heart's valves and is commonly associated with disease. Conditions affecting the normal functioning of the mitral valve include, for example, mitral valve regurgitation, mitral valve prolapse, and mitral valve stenosis. Mitral valve regurgitation refers to the condition whereby the leaflets of the mitral valve fail to coapt into apposition during ventricular contraction, resulting in abnormal leaking of blood from the left ventricle into the left atrium. Mitral valve prolapse refers to the condition where the mitral leaflets bulge abnormally up into the left atrium causing irregular behaviour of the mitral valve. Mitral valve stenosis refers to the narrowing of the heart's mitral valve obstructing blood flow. A number of factors may affect the normal functioning of the mitral leaflets.

Although intermediate grades of impaired functioning of the mitral valve may not require treatment, severely impaired mitral valve function may result in symptoms (for example, breathlessness, fatigue, exercise intolerance), and may represent a threat to life expectancy. Often, invasive surgery must be performed to repair or replace an abnormal mitral valve.

Traditionally, repairing or replacing a mitral valve involves an open heart procedure. Open heart procedures present patients with morbidity and mortality risks and require a post-op period of convalescence that is typically several months in duration. Open heart surgery may pose prohibitive risks, or may otherwise not be ideal for some patients, including some elderly patients and patients with other health issues. Repairing or replacing the mitral valve without invasive open heart procedures may be attractive therapy for such patients.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides an apparatus for repairing or replacing a mitral valve, in particular for clamping a mitral valve of a heart. The apparatus comprises an atrial band securable to a ring-shaped ventricular band. The ventricular band comprises an anterior band and a posterior band connectable to the anterior band. The atrial and anterior bands each have a pair of apertures. Each of the apertures is positioned proximate to a respective terminal end of the bands. The apertures of the atrial and anterior bands are arranged to align with one another when the inner surface of the atrial band engage with the inner surface of the anterior band. Means are provided to secure the atrial band to the anterior band when their inner surfaces engage.

One aspect of the invention provides a method for repairing or replacing a mitral valve. The method comprises the steps of advancing a first guide wire intravascularly through towards a ventricular surface of a mitral valve leaflet in the ventricular space, advancing a ventricular band along the first guide wire, encircling the ventricular band around the mitral valve leaflet, extending a second and third guide wire from a pair of apertures defined by an anterior band of the ventricular band, advancing the second and third guide wires through the mitral valve leaflet sequentially, advancing an atrial band along the second and third guide wires, and securing the atrial band to the anterior band.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 6A is a front elevational view of an atrial band of the FIG. 4 apparatus in its natural, undeformed, state. FIG. 6B is a top perspective view of an atrial band of the FIG. 4 apparatus in its natural, undeformed, state. FIG. 6C is a front elevational view of an atrial band of the FIG. 4 apparatus in its natural, undeformed, state. FIG. 6D is a top perspective view of an atrial band of the FIG. 4 apparatus in its natural, undeformed, state. FIG. 6E is a front elevational view of an atrial band of the FIG. 4 apparatus in its natural, undeformed, state. FIG. 6F is a top perspective view of an atrial band of the FIG. 4 apparatus in its natural, undeformed, state.

FIG. 7 is side perspective view showing an example locking mechanism for securing the ventricular band of the FIG. 4 apparatus.

FIG. 8 is side perspective view showing an example locking mechanism for securing the ventricular band of the FIG. 4 apparatus.

FIG. 9 is side perspective view showing an example locking mechanism for securing the ventricular band of the FIG. 4 apparatus.

FIG. 10 is side perspective view showing an example locking mechanism for securing the ventricular band of the FIG. 4 apparatus.

FIGS. 11A to 11F are schematic illustrations showing the steps of assembling the FIG. 4 apparatus into an implanted configuration.

FIG. 19A is a top plan view, partly cutaway, of a ventricular band of the FIG. 4 apparatus. FIG. 19B is a top plan view, partly cutaway, of the ventricular band of FIG. 19A. FIG. 19C is a side elevational view, partly cutaway, of ventricular band of FIG. 19A.

FIGS. 21A to 21L are schematic illustrations showing the steps of implantation of the FIG. 4 apparatus in the heart.

FIGS. 24A to 24F are schematic illustrations of an example catheter for use in the implantation of the FIG. 4 apparatus. FIG. 24A-A is an isolated plan view showing the distal end of the example catheter with the septum removed. FIG. 24A-B is an isolated side view showing the septum of the example catheter. FIG. 24A-C is an isolated plan view showing the distal end of an example catheter with the septum inserted within the body of the catheter. FIG. 24A-D is an isolated side view showing the curved distal portion of the example catheter, showing a slot in continuity the afferent channel of the catheter.

FIGS. 25A to 25F are schematic illustrations of an example catheter for use in the implantation of the FIG. 4 apparatus. FIG. 25A-A is an isolated plan view showing the distal end of the example catheter with the septum removed. FIG. 25A-B is an isolated side view showing the septum of the example catheter. FIG. 25A-C is an isolated plan view showing the distal end of an example catheter with the septum inserted within the body of the catheter. FIG. 25A-D is an isolated side view showing the curved distal portion of the example catheter.

FIG. 28A is a top perspective view of the FIG. 4 apparatus with a central guide wire extending therefrom. FIG. 28B is a top perspective view of the FIG. 4 apparatus, showing a cutting device guided into position by the central guide wire. FIG. 28C is side view of FIG. 28B.

FIG. 29A is a top perspective view of the FIG. 4 apparatus with a central guide wire extending therefrom. FIG. 29B is a top perspective view of the FIG. 4 apparatus, showing a cutting device guided into position by the central guide wire. FIG. 29C is side view of FIG. 28B.

DESCRIPTION

Figure 1:
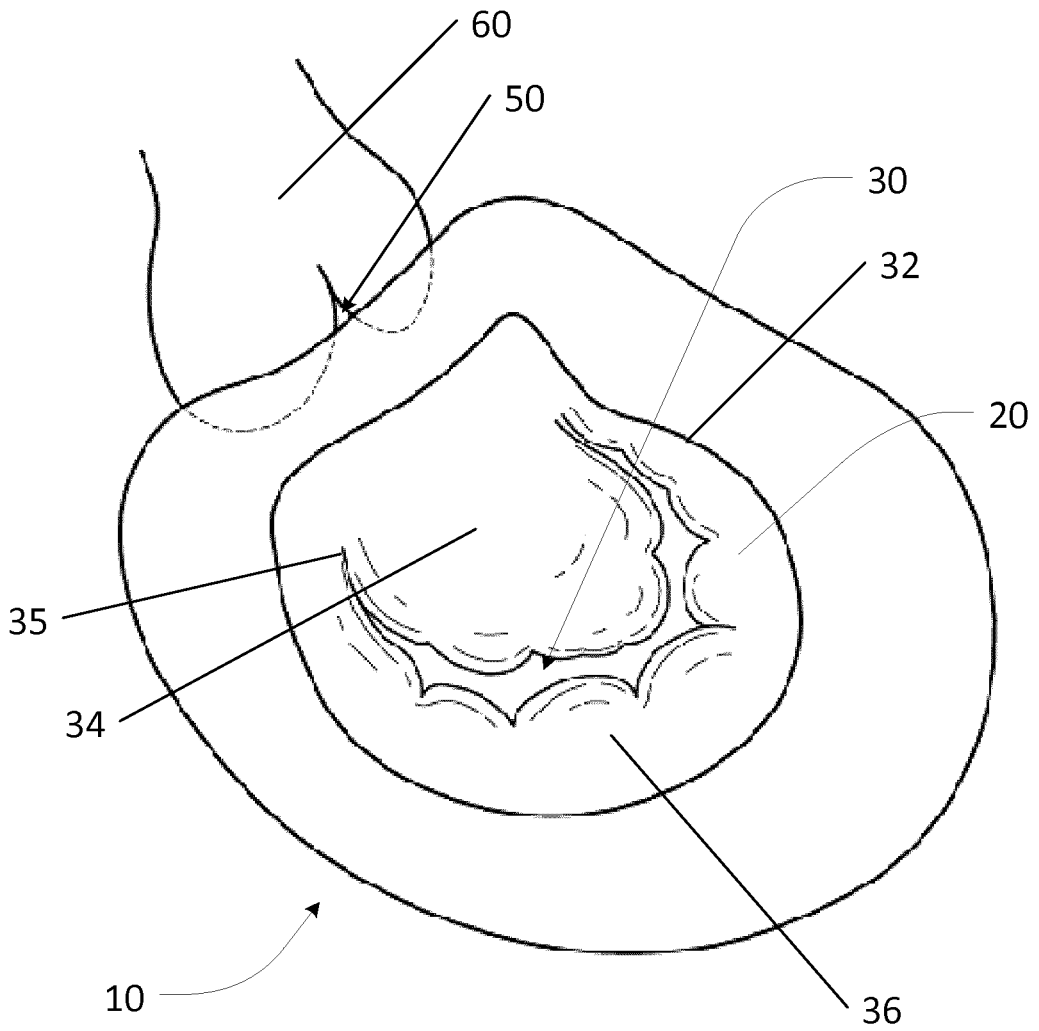
FIG. 1 is a top cross-sectional view of a heart showing normal coaptation of a mitral valve.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless context dictates otherwise, the term "anterior" (as used herein in relation to a patient's body and parts thereof) refers to a position that is more near the front surface of the patient's body or part thereof than the rear surface of the patient's body or part thereof.

Unless context dictates otherwise, the term "posterior" (as used herein in elation to a patient's body and parts thereof) refers to a position that is more near the rear surface of the patient's body or part thereof than the front surface of the patient's body or part thereof.

Unless context dictates otherwise, the terms "percutaneous", "percutaneously", and the like (as used herein) refer to a method of accessing a patient's circulatory system and/or heart through the skin, such as by needle access.

Unless context dictates otherwise, the term "antegrade" (as used herein) refers to a percutaneous approach to a mitral valve via the femoral vein, right atrium, atrial septal puncture, and left atrium (i.e. in the normal direction of blood flow through a patient's circulatory system).

Unless context dictates otherwise, the term "retrograde" (as used herein) refers to a percutaneous approach to the mitral valve via the femoral artery, wherein the left ventricle is accessed via the aortic valve (i.e. in reverse of the normal direction of blood flow through a patient's circulatory system).

Unless context dictates otherwise, the term "intravascular" (as used herein) means situated or occurring with a blood vessel or circulatory system.

Unless context dictates otherwise, the term "external" (as used herein in relation to a patient's body and parts thereof) means situated outside of a patient's circulatory system or body.

Unless context dictates otherwise, the term "transcatheter" (as used herein) refers to a method performed through the lumen of a catheter.

Unless context dictates otherwise, the term "circulatory system" (as used herein) refers to a system that circulates blood and/or lymph through a patient's body, consisting of one or more of the heart, blood vessels, blood, lymph, and the lymphatic vessels and glands.

Unless context dictates otherwise, the term "afferent" means towards the operator and away from the patient's circulatory system or body.

Unless context dictates otherwise, the term "efferent" means away from the operator and towards the patient's circulatory system or body.

Although the methods and apparatus of the present invention may be used for the percutaneous repair of any of the cardiac valves, the following description will focus on the repair of mitral valves. Further, while the methods and apparatus of the present invention will preferably be percutaneous and intravascular, such methods and apparatus may be used for performing open heart surgery where the heart is accessed through the myocardial tissue and/or in minimally invasive procedures where access to the heart is achieved thorascopically. Further still, while the methods and apparatus of the present invention may be used with conventional transcatheter valve prostheses, such methods and apparatus may be used with prostheses implanted through the myocardial tissue of the heart and/or prostheses implanted using minimally invasive procedures where access to the heart is achieved thorascopically.

Figure 2:
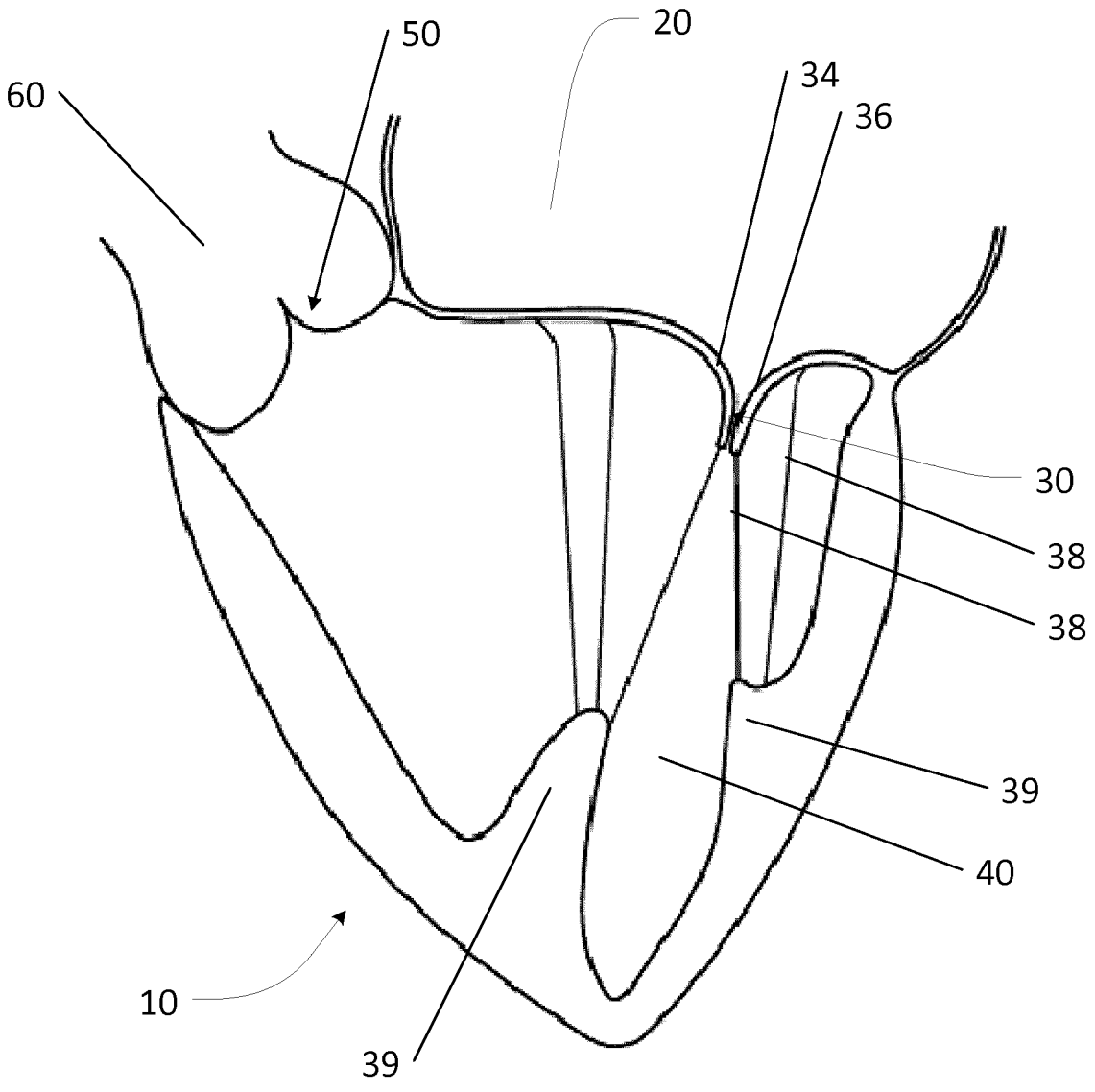
FIG. 2 is a side elevational cross-sectional view of the heart shown in FIG. 1.

The human heart 10, shown in FIGS. 1 and 2 is a muscle pump which relies on heart valves to achieve blood flow. In normal physiology, oxygenated blood returning from the lungs is collected in a left atrium 20, and then passes through a mitral (inlet) valve 30 to enter a left ventricle 40 (i.e. the pumping chamber). With contraction of left ventricle 40, the elevation of left ventricular pressure causes mitral valve 30 to close (FIGS. 1 and 2), preventing reversal of blood flow back into atrium 20. As ventricular pressure exceeds aortic pressure, aortic (outlet) valve 50 opens, and blood is pumped forward into aorta 60. When left ventricle 40 relaxes, the ventricular pressure drops, mitral valve 30 reopens to permit flow of blood from left atrium 20 to left ventricle 40, and the process repeats.

Mitral valve 30 separates left atrium 20 from left ventricle 40, and is comprised of a mitral annulus 32, leaflets (anterior 34 and posterior 36), chordae tendinae 38, and papillary muscles 39. During ventricular contraction (systole), the ventricular pressure rises, which forces displacement of mitral leaflets 34, 36 towards atrium 20 (i.e. commonly known as atrial or leaflet displacement). The length and integrity of chordae tendinae 38 determines the degree of leaflet displacement. In normal physiology, equal displacement of anterior mitral leaflet 34 and posterior mitral leaflet 36 results in contact (coaptation) between the leaflets, and consequent competence of mitral valve 30.

Figure 3:
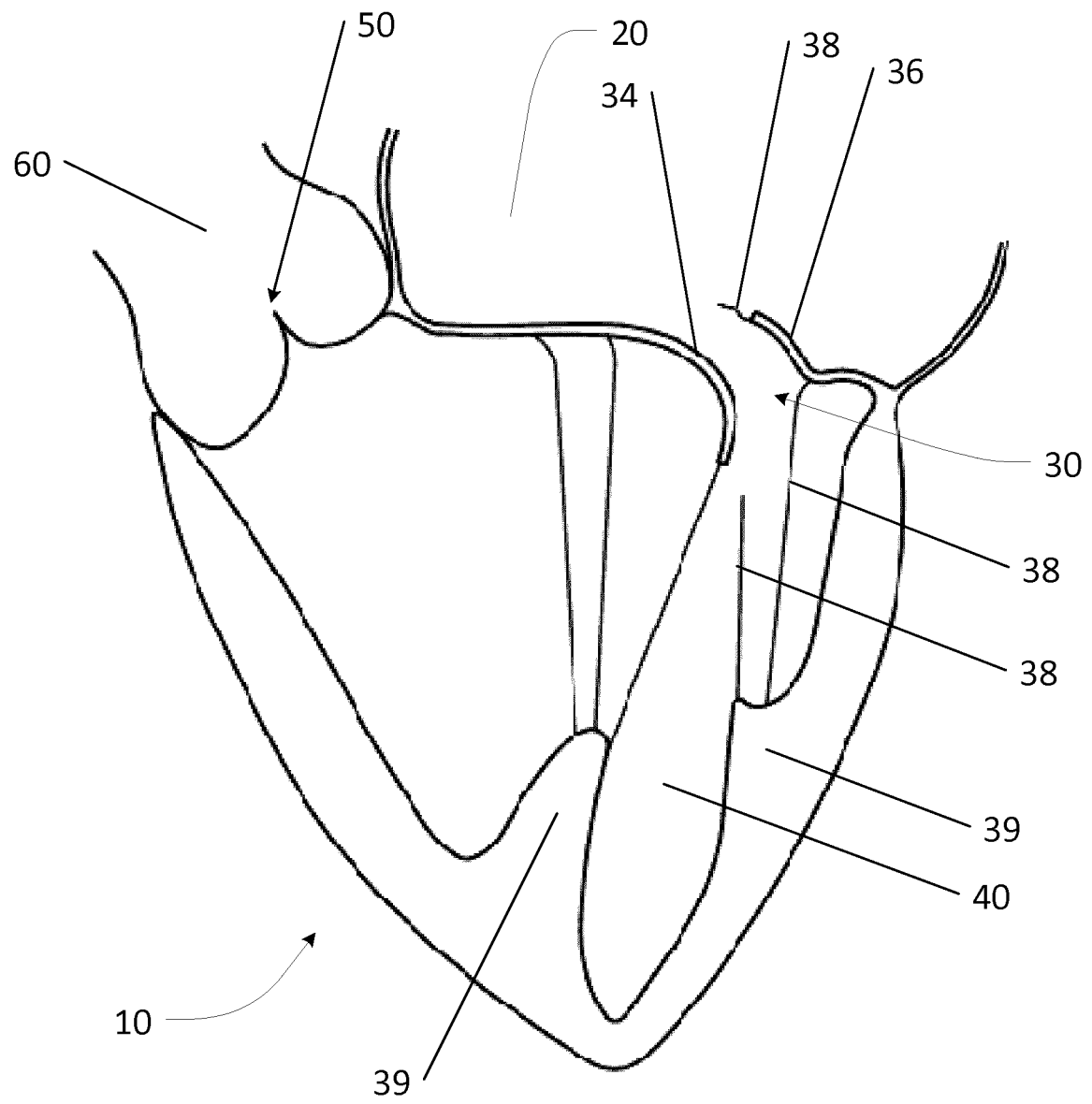
FIG. 3 is a side elevational cross-sectional view of a heart showing prolapse of a posterior mitral valve leaflet.

In circumstances where mitral leaflet 34 and/or 36 is supported by chordae tendinae 38 which are elongated or ruptured, ventricular contraction may result in excessive atrial displacement of the leaflet(s), and this may prevent coaptation between the leaflets (FIG. 3). This is referred to as mitral leaflet prolapse. In this circumstance, the competency of mitral valve 30 may be compromised and leakage may occur. Leakage through the mitral valve is referred to as mitral regurgitation, and when it is due to mitral leaflet prolapse it is referred to as degenerative mitral regurgitation. In other circumstances, the ventricular muscle itself can be diseased and its function impaired causing limited ventricular contraction and progressive ventricular dilation. Since mitral leaflets 34, 36 are attached by chordae tendinae 38 to the ventricular muscle, ventricular dilation can limit leaflet movement toward atrium 20 during contraction, resulting in poor leaflet coaptation and causing mitral regurgitation. This is referred to as functional mitral regurgitations.

The methods and apparatus of example embodiments of the present invention use existing transcatheter heart valve prostheses to percutaneously replace a mitral valve. The methods and apparatus of example embodiments of the present invention may be used to precisely secure the mitral valve leaflet (e.g., anterior mitral valve leaflet) in position during transcatheter mitral valve replacement (TMVR) procedures. This may facilitate precise percutaneous incision of the anterior mitral valve leaflet, prevents the anterior mitral valve leaflet from tearing, and avoids separation between the valve leaflet and the implanted TMVR prosthesis.

Figure 4:
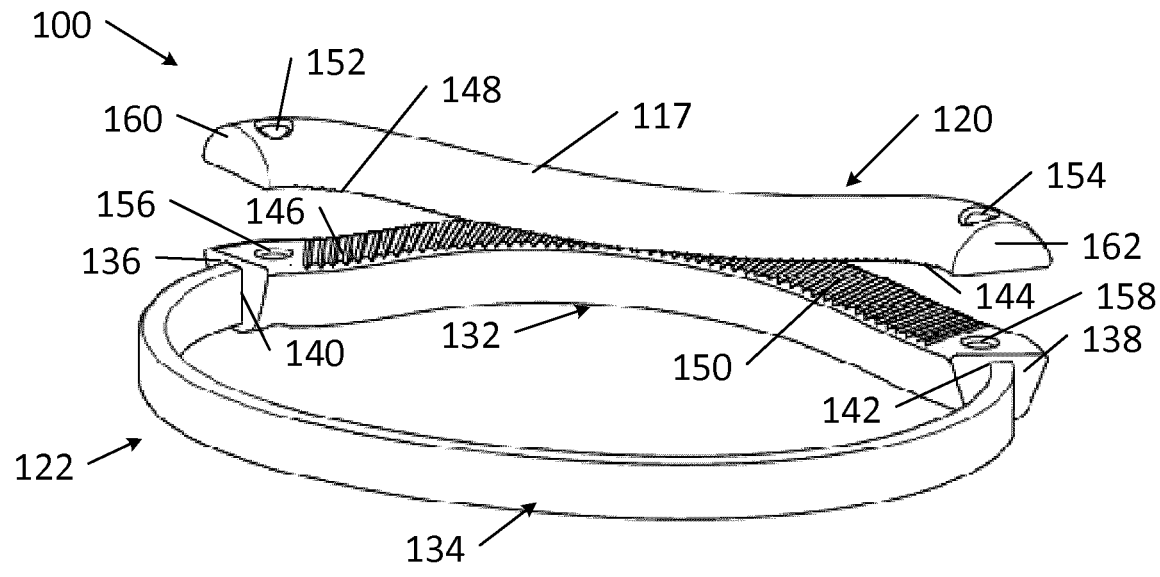
FIG. 4 is a top perspective view of an apparatus for use in replacing or repairing a mitral valve in an unsecured configuration according to an example embodiment.
Figure 5:
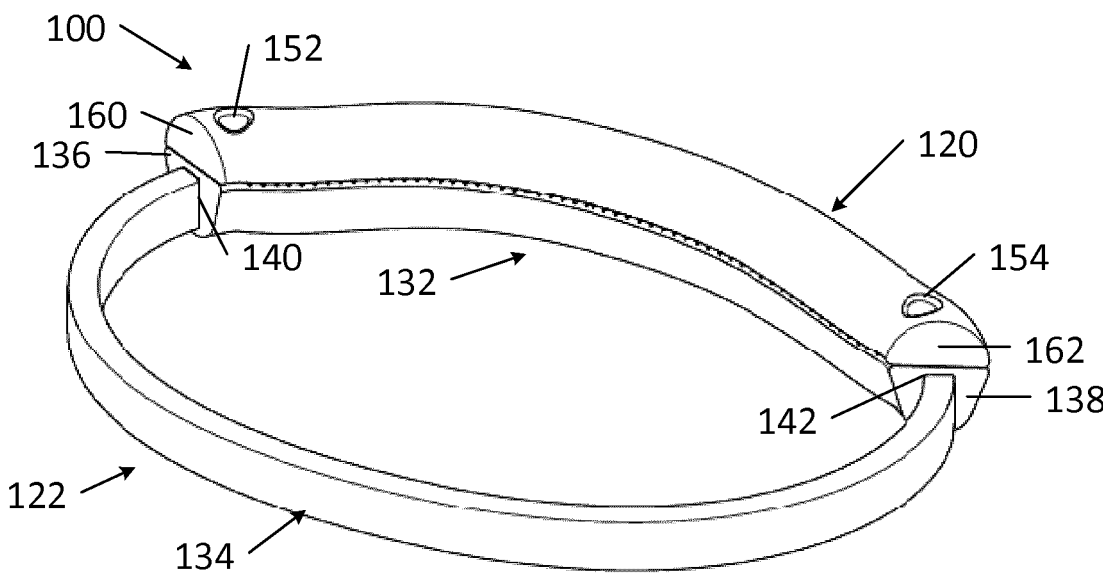
FIG. 5 is a top perspective view of the FIG. 4 apparatus in an implanted configuration.

Referring to FIGS. 4 and 5, in one embodiment the apparatus of the invention is an apparatus 100 for clamping a mitral valve of a heart. Apparatus 100 has an elongated, flexibly deformable, atrial band 120 securable to a ring-shaped ventricular band 122. Ventricular band 122 has an elongated, flexibly deformable, anterior band 132 with opposing terminal ends 136, 138 respectively connected to opposing terminal ends 140, 142 of an elongated, flexibly deformable, posterior band 134 to form a closed ring. Atrial band 120 and anterior band 132 are arranged to press against a mitral valve leaflet, such as an anterior mitral valve leaflet, from opposing atrial and ventricular sides of the heart. Posterior band 134 is arranged to encircle around the sub-mitral space below the mitral valve leaflet on the ventricular side. Anterior 132 and posterior 134 bands each define a channel 126, 222 which extends longitudinally through its length, providing a passageway for guide wires to travel through the bands (as best seen in FIGS. 20A-20F). Inner surfaces 144, 146 of the respective atrial band 120 and anterior band 132 are dimensioned to contact one another, along their lengths, to arrange apparatus 100 into an implanted configuration (as seen in FIG. 5). Grippers 148, 150, such as outwardly projecting gripping teeth, may be arranged on inner surfaces 144, 146 to enhance contact with the mitral valve leaflet therebetween.

FIG. 4 illustrates apparatus 100 in an unsecured configuration where atrial band 120 is disengaged from anterior band 132 of ventricular band 122. In the unsecured configuration, atrial 120 and anterior 132 bands are in a natural, undeformed, state. In the implanted configuration, atrial 120 and anterior 132 bands are in a deformed state (as seen in FIG. 5).

In the natural states, atrial band 120 and/or anterior band 132 of ventricular band 122 may assume an annular curvature along its length, such that bands 120, 132 may be hyperbolic-shaped. When apparatus 100 is delivered into the heart, the annular curvatures of the bands 120, 132 are in the plane of the mitral annulus, arranged to correspond with the annular circumference of the anterior mitral annulus.

In the natural states, the inner surfaces 144, 146 of one or both of atrial band 120 and anterior band 132 of ventricular band 122 may assume a curvature with respect to the axial plane of apparatus 100. The axial plane is defined by an imaginary plane that divides apparatus 100 into atrial band 120 and ventricular band 122. In some embodiments, the degrees of curvature of one or both of inner surfaces 144, 146 of the respective atrial band 120 and anterior band 132 are about 0°, i.e., one or both of inner surface(s) 144, 146 are substantially planar, parallel to the axial plane of apparatus 100. In some embodiments, the degrees of curvatures of inner surfaces 144, 146 of the respective one or both of atrial band 120 and anterior band 132 are greater than 0° with the vertex of the curvature being at a midpoint along the length of atrial band 120 and/or anterior band 132. In such embodiments, one or both of inner surface(s) 144, 146 of atrial 120 and anterior 132 bands are convex-shaped, i.e., the pair of opposing edges extending along the length of one or both of inner surface(s) 144, 146 of atrial 120 and anterior 132 bands are curved outwardly from an imaginary line that is parallel to the axial plane of the apparatus such that one or both inner surface(s) 144, 146 may define a U-shape configuration and/or an inverted U-shape configuration. In some embodiments, inner surface 144 of atrial 120 has a U-shape configuration and inner surface 146 of anterior band 132 has an inverted U-shape configuration.

FIGS. 6A-6F illustrate the different shapes that inner surfaces 144, 146 of atrial 120 and anterior 132 bands can assume in their natural states. Inner surface(s) 144, 146 of atrial band 120 or anterior band 132 may be substantially planar in the axial plane of apparatus 100 (FIGS. 6A, 6B), curved having a U-shape configuration in the axial plane of apparatus 100 (FIGS. 6E, 6F) or curved having an inverted U-shape configuration in the axial plane of apparatus 100 (FIGS. 6C, 6D). In their natural states, inner surfaces 144, 146 of atrial 120 and anterior 132 bands can have the same shape or have different shapes.

Atrial 120 and anterior 132 bands may be made of the same or different materials, including for example silicone, medical grade plastic, thermal plastic, stainless steel, metal, a metal alloy (e.g., nitinol or another nickel or titanium alloy), and titanium. Atrial 120 and anterior 132 bands may be made of materials with equal stiffness, i.e., stiffness being the extent to which the bands resist deformation in response to an applied force, typically measured in Young's modulus (E); the stiffer the material, the more resistant it is to deformation, the greater the Young's modulus. Atrial 120 and anterior 132 bands may alternatively be made of materials with different stiffnesses.

In one embodiment, inner surfaces 144, 146 of atrial 120 and anterior 132 bands are deformed to assume a curvature with respect to the axial plane of apparatus 100 when apparatus 100 is in the implanted configuration (as best seen in FIG. 5). Atrial 120 and anterior 132 bands that are constructed from materials of different stiffness facilitate the strengthening of the connection of bands 120, 132 at their inner surfaces 144, 146 thereby strengthening the connection of bands 120, 132 onto opposing atrial and ventricular sides of the mitral valve leaflet. Bands 120, 132 of different stiffness act on one another upon application of a continuous compressive force such that the inner surfaces 144, 146 press against each other thereby deforming the bands into the same resultant shape when the bands 120, 132 are secured to one another.

In some embodiments, the relatively more flexible band (e.g., the band having a material with a lower Young's modulus) deforms to conform to the shape of the stiffer band (e.g., the band having a material with the higher Young's modulus) when the bands are secured. In one embodiment, a generally planar inner surface 144 of atrial band 120 (see FIGS. 6A-B) is constructed of a material that is more flexible than a curved inner surface 146 of anterior band 132 (see e.g., FIGS. 6C to 6F; the Young's modulus of inner surface 144 of atrial band 120 is lower than the Young's modulus of inner surface 146 of anterior band 132). In such embodiment, the generally planar inner surface 144 of atrial band 120 deforms to conform to the curved inner surface 146 anterior band 132 upon continuous application of a compressive force on the atrial band 120 against anterior band 132 in the implanted configuration, resulting in a curved resultant shape (i.e., in the implanted configuration, the shapes of inner surfaces 144, 146 of atrial 120 and anterior band 132 are identical). The curved resultant shape of the inner surfaces 144, 146 of the secured bands 120, 132 provide a consistent gripping force along the lengths of the atrial 120 and anterior 132 bands onto opposing sides of the mitral valve leaflet.

Both inner surfaces 144, 146 of bands 120, 132 may be curved. The two curved bands of different stiffness may deform into a generally planar or a curved resultant shape, with a desired curvature, in the implanted configuration.

Atrial band 120 is defined by a pair of apertures 152, 154 each one positioned proximate to one of the terminal ends 160, 162. Anterior band 132 is defined by a pair of apertures 156, 158 each one positioned proximate to one of the terminal ends 136, 138, apertures 156, 158 correspond in position with the respective apertures 152, 154 defined by atrial band 120 (i.e., in the implanted configuration, aperture 152 of atrial band aligns with aperture 156 of anterior band and aperture 154 of atrial band aligns with aperture 158 of anterior band). Apertures 152 and 156, and apertures 154 and 158 defined by the corresponding atrial band 120 and anterior band 132 provide a site of origin for guide wires 194, 196 respectively (best seen in FIG. 12). A pair of locking members 164, 166, delivered to the site of implantation by guide wires 194, 196, are arranged to secure atrial band 120 to anterior band 132 by insertion through a respective aperture set 152, 156 and aperture set 154, 158 (as seen in FIGS. 11E and 11F).

Figure 14:
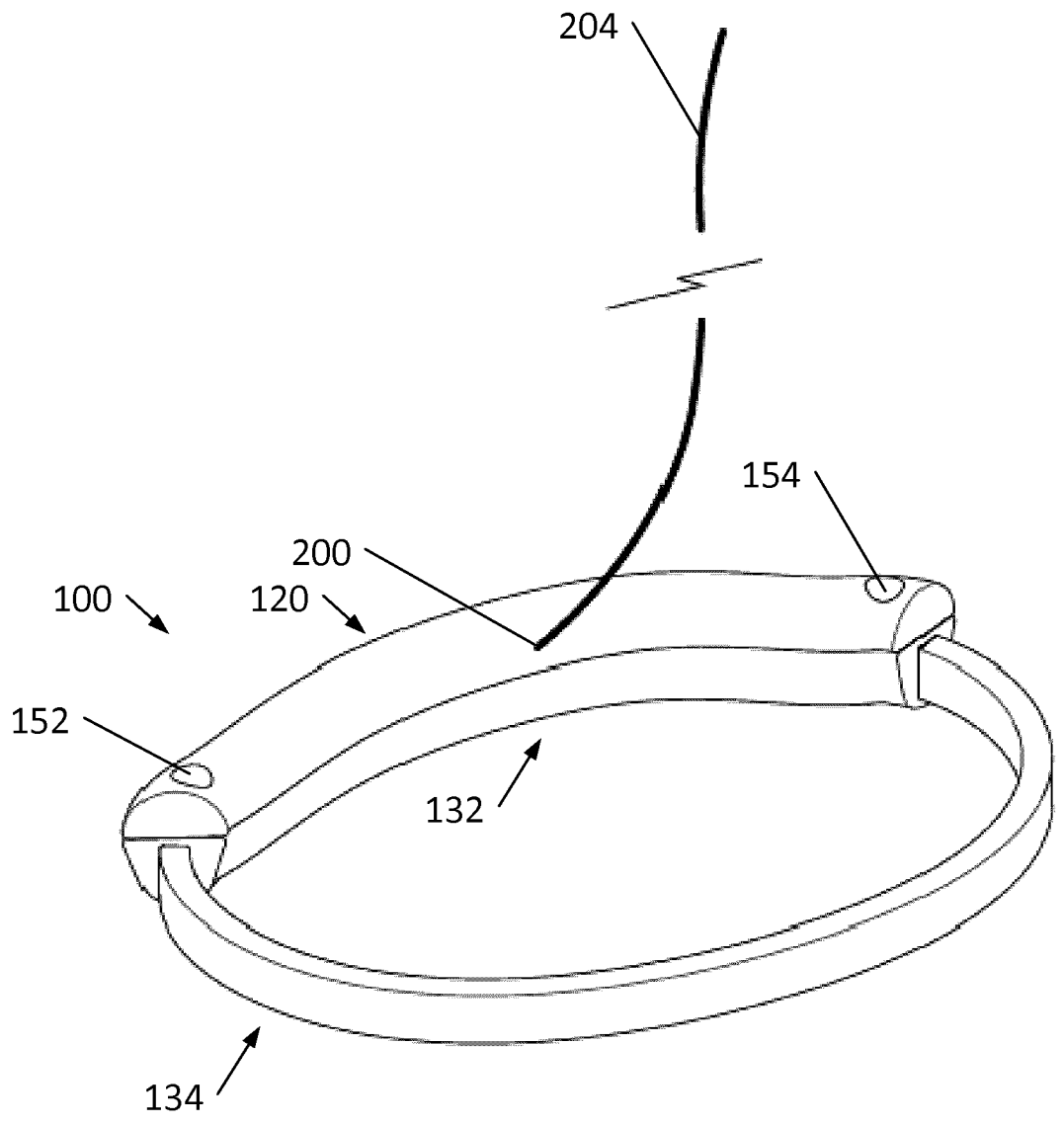
FIG. 14 is top perspective view of the FIG. 4 apparatus showing a central guide wire extending therefrom.
Figure 15:
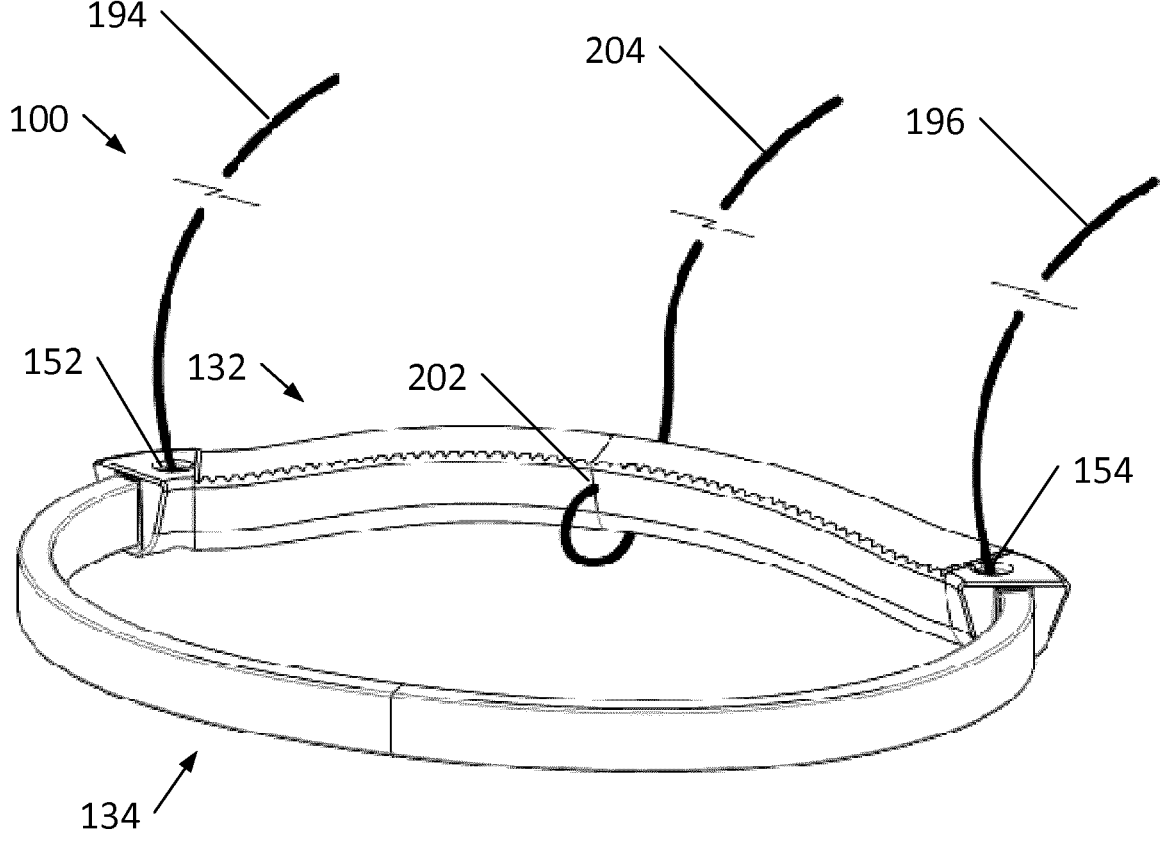
FIG. 15 is top perspective view of a ventricular band the FIG. 4 apparatus showing guide wires extending therefrom.

Referring to FIGS. 14 and 15, in some embodiments, atrial 120 and anterior 132 bands are each defined by a respective central aperture 200, 202 positioned midway between apertures 152, 154 of atrial band 120 and apertures 156, 158 of anterior band 132. Central apertures 200, 202 correspond in positions on the respective atrial 120 and anterior 132 bands so that the apertures align when atrial 120 and anterior 132 bands are secured. Central apertures 200, 202 provide a site of origin for a central guide wire 204 to extend therefrom. Central guide wire 204 facilitates precise positioning of a cutting device in a mitral valve replacement or repair procedure for incising a native mitral valve leaflet. In some embodiments, central aperture 200 is positioned on the same plane as apertures 152, 154 (FIG. 14). The central guide wire 204 that extends from central aperture 200 may be used to position the cutting device that is introduced from above the native mitral valve (i.e., from the atrium of the heart) to incise the native mitral valve leaflet. In some embodiments, central aperture 202 is positioned on a plane offset from the plane of apertures 152, 154, 156, 158 (FIG. 15). Referring to FIG. 15, central aperture 202 is defined on a surface of anterior band 132 facing posterior band 134. The central guide wire 204 that extends from central aperture 202 may be used to position the cutting device that is introduced from below the native mitral valve (i.e., from the ventricle of the heart) to incise the native mitral valve leaflet.

Figures 16A, 16B, 16C, 16D:
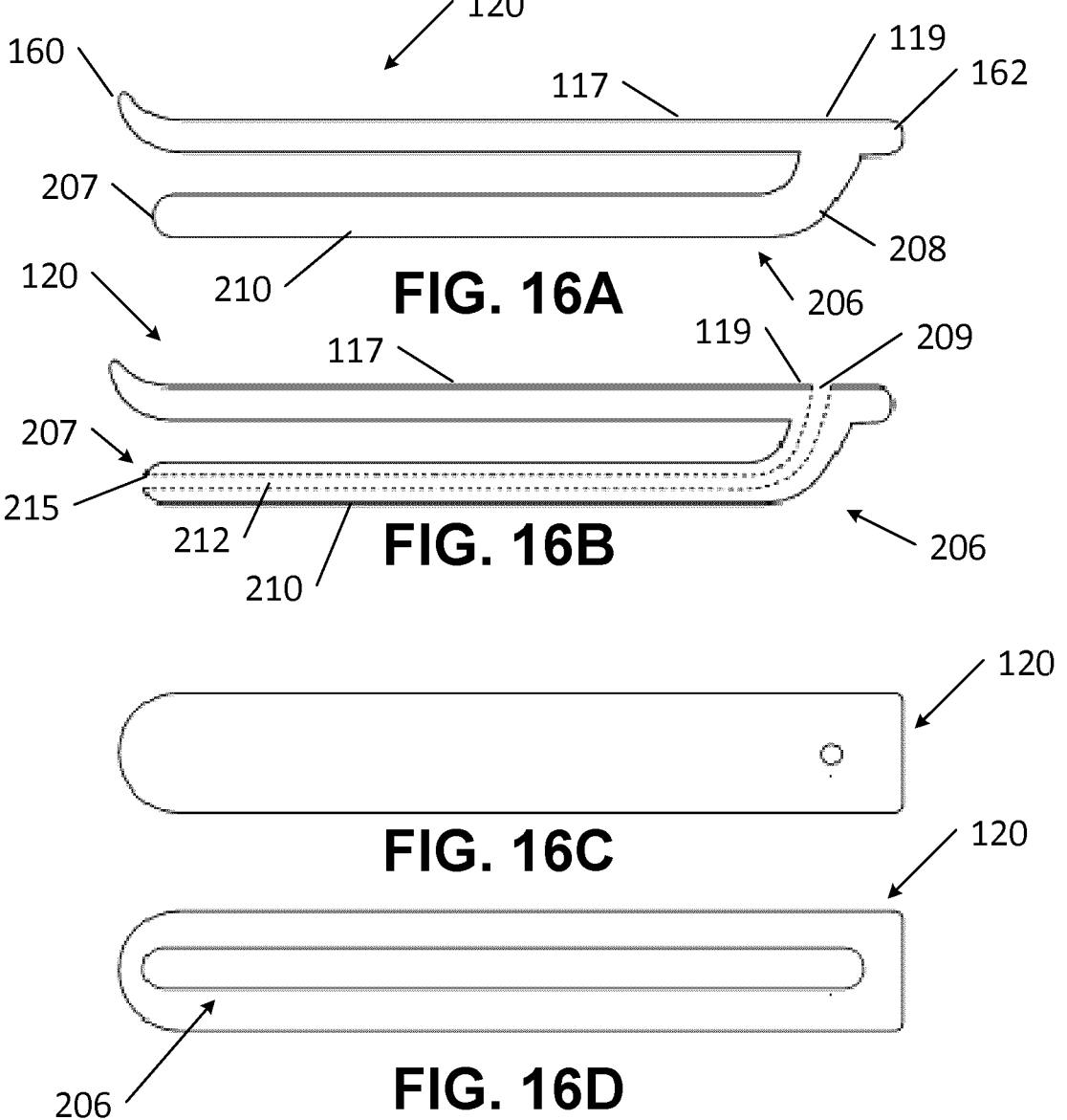
FIG. 16A is a side elevational view of an atrial band of the FIG. 4 apparatus.
FIG. 16B is a side elevational view, partly cutaway, of the FIG. 16A atrial band.
FIG. 16C is top plan view of the FIG. 16A atrial band.
FIG. 16D is a bottom plan view of the FIG. 16A atrial band.
Figures 17A, 17B:
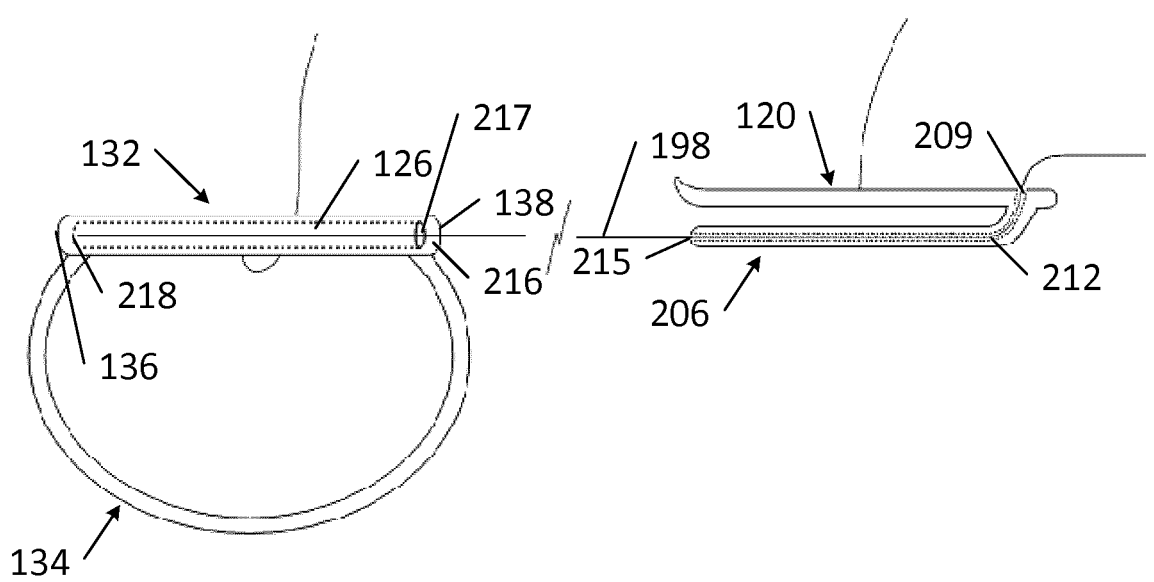
FIG. 17A is a top plan view, partly cutaway, of a ventricular band of the FIG. 4 embodiment.
FIG. 17B is a side elevational view, partly cutaway, of an atrial band of the FIG. 4 embodiment.

In some embodiments, an attachment member 206 is provided to facilitate the connection between atrial band 120 and anterior band 132. Referring to FIGS. 16A-16D and 17A-17B, an elongated attachment member 206, integral with atrial band 120, extends longitudinally from a portion 119 of atrial band 120 proximate to one of terminal ends 160, 162, to a tapered terminal end 207 of attachment member 206. Attachment member 206 has a curved section 208, connected to portion 119, extending to a straight section 210 which is parallel to atrial band 120. A channel 212 extends from an opening 209, defined by an upper surface 117 of atrial band 120 proximate to portion 119, to an opening 215 at terminal end 207, to provide a passageway for guide wires to extend therethrough (as best seen in FIG. 16B).

Figure 18A:
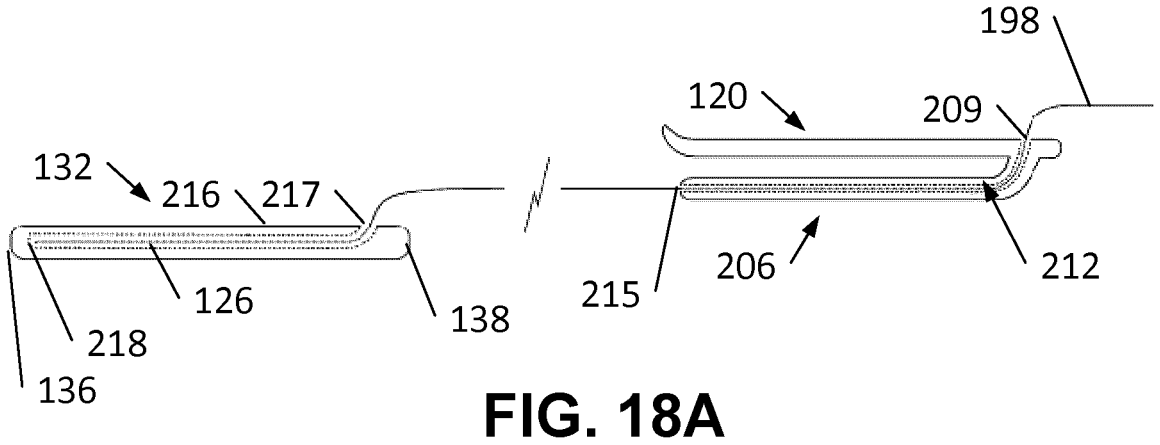
FIG. 18A are side elevational views, partly cutaway, of an anterior band and an atrial band of the FIG. 4 embodiment.
Figure 18B:
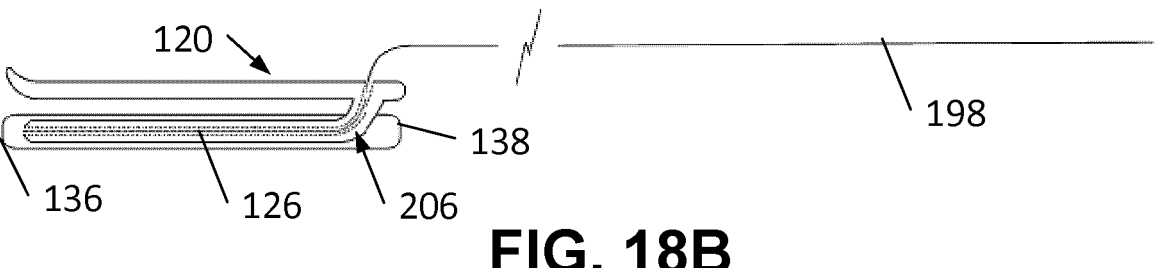
FIG. 18B are side elevational views, partly cutaway, of the FIG. 18A atrial band being secured to the anterior band.
Figures 20A, 20B, 20C, 20D, 20E, 20F:
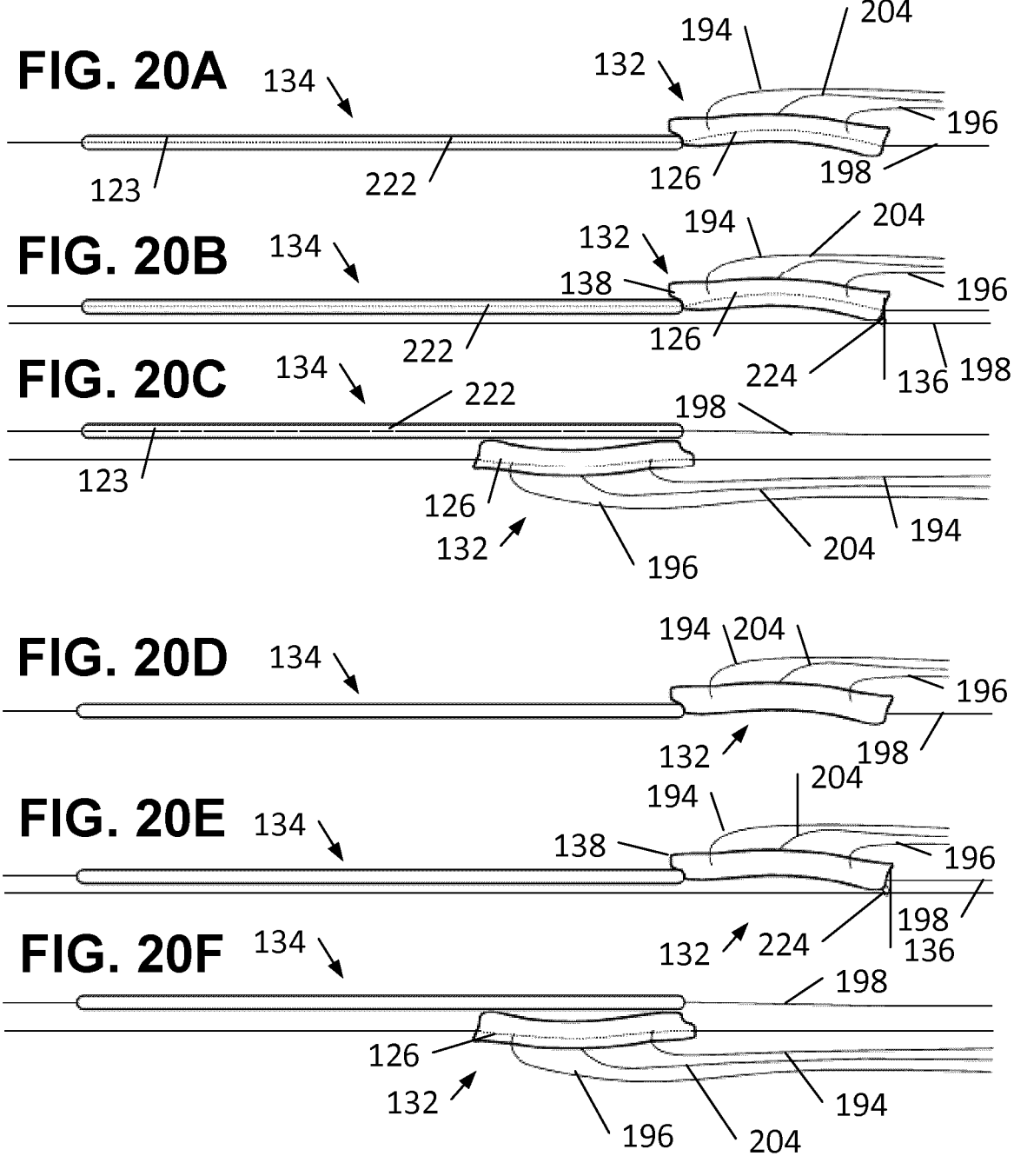
FIGS. 20A to 20F are schematic illustrations showing the arrangement of guide wires along the channels within the FIG. 4 apparatus.

As best seen in FIGS. 18A-18B, attachment member 206 is insertable into a channel 126 defined within anterior band 132 along a length thereof for securing atrial band 120 to anterior band 132. Channel 126 extends from an opening 217, defined by an upper surface 216 of anterior band 132, to a closed end 218 proximate to one of the terminal ends 136, 138 of anterior band 132 (as best seen in FIGS. 19A-19C). Referring to FIGS. 18A-18B, to guide attachment member 206 into position within channel 126 of anterior band 132, a guide wire 198 may be arranged to extend along the length of channel 126 of anterior band 132 from closed end 218 and out through opening 217 to extend through the length of channel 212 of attachment member 206, entering into opening 215 and exiting from opening 209 of atrial band 120.

Means are provided for securing anterior band 132 to posterior band 134 of ventricular band 122 to form a closed ring. FIGS. 7-10 are example embodiments of locking mechanisms that can be employed. In the FIGS. 7 and 8 embodiments, posterior band 134 has a U-shaped hook 168 which extends from its terminal end 140 and anterior band 132 has a closed loop 170 which extends from its terminal end 136. In some embodiments, U-shaped hook 168 directly latches onto closed loop 170 to secure posterior band 134 to anterior band 132 (as seen in FIG. 7). In some embodiments, a guide wire is provided to extend out from inner channel 222 of posterior band 134 through the terminal end 140 for looping around the closed loop 170 of the anterior band 132 to secure the bands 134, 132 (as seen in FIG. 8).

In the FIG. 9 embodiment, anterior band 132 has a slot 172 at its terminal end 136 shaped to snugly receive terminal end 140 of posterior band 134. Terminal end 140 comprises a projection 174, with opposing bevel side edges 176, 178, protruding outwardly from opposing sides 180, 182 of the band 134.

In the FIG. 10 embodiment, the terminal ends 136, 140 of the respective anterior band 132 and posterior band 134 each defines a respective wedge-shaped slot 184, 186 shaped to snugly receive a connector 188. Connector 188 has two wedge-shaped connecting members 190A, 190B shaped to insert into the respective wedge-shaped hole 184, 186 so as to secure anterior band 132 to posterior band 134.

FIGS. 7-10 illustrate embodiments which has a locking mechanism provided at only one terminal end of each of the anterior and posterior bands (i.e., the anterior and posterior bands are securable only at one terminal end; the other terminal end of the anterior and posterior bands are fixedly secured). This is not mandatory; locking mechanisms may be provided at both terminal ends of the anterior and posterior bands (i.e., the anterior and posterior bands are securable at both terminal ends).

In some embodiments, the average width of anterior band 132 is greater than the average width of posterior band 134 (i.e., the cross-sectional area of anterior band 132 is greater than the cross-sectional area of posterior band 134). The average width of anterior band 132 may be about two to three times greater than the average width of posterior band 134.

In some embodiments, the cross-sectional shape of posterior band 134 is a quadrilateral with four right angles (i.e., the angle bounded by each of the two sides is 90°). The right angled quadrilateral cross-sectional shape facilitates flexing of posterior band 134 in the radial direction of the apparatus 100 while restricting flexing in the axial direction. Movement in the radial plane is desirable to ensure a snug fit between the transcatheter heart valve (THV) and the posterior band 134 when the THV is implanted. Lack of movement in the axial direction is desirable to ensure that the posterior band remains in the posterior submitral space as close to the mitral annulus as possible, minimizing any downward or apical movement toward the ventricular apex or away from the annulus, to ensure that the posterior band is covered with the posterior mitral valve leaflet. This creates a seal between the THV and the apparatus with the mitral valve leaflet.

Posterior band 134 may be made of any suitable biocompatible material, such as silicone, medical grade plastic, thermal plastic, stainless steel, metal, a metal alloy (e.g., nitinol or another nickel or titanium alloy), and titanium.

Anterior 132 and posterior 134 bands may be constructed from a single continuous band. Anterior 132 and posterior 134 bands may alternatively be constructed from a plurality of modular units 192 which are arranged contiguously to create the closed ring shape (as best shown in FIG. 11A-F). Modular units 192 bend about each other, facilitating the flexing and deformation of ventricular band 122 along the length thereof.

Figure 12:
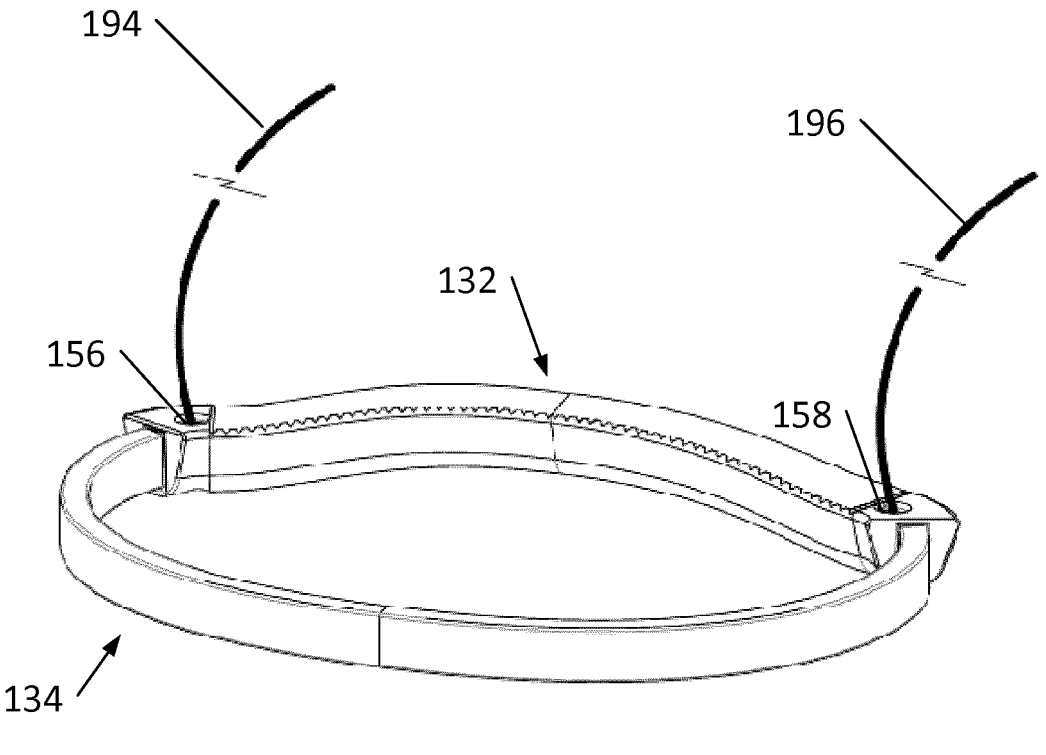
FIG. 12 is a top perspective view of a ventricular band of the FIG. 4 apparatus showing guide wires extending therefrom.
Figure 13:
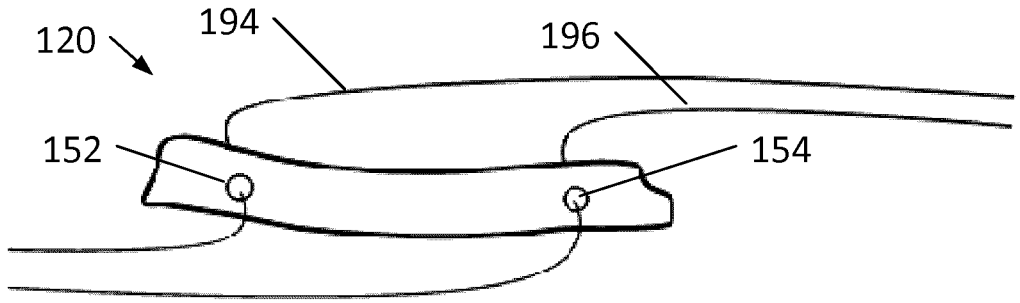
FIG. 13 is top plan view of an atrial band of the FIG. 4 apparatus showing guide wires extending therefrom.

Tether (i.e., cuttable) guide wires are used to position apparatus 100 at the desired implantation site. Referring to FIGS. 12 and 13, a pair of guide wires 194, 196 are arranged to extend through or from apertures 156, 158 defined by anterior band 132. Guide wires 194, 196 are arranged to extend through apertures 152, 154 of atrial band 120 for positioning atrial band 120 on top of anterior band 132. A longitudinally-extending guide wire 198 is arranged to extend through the lengths of the channel 123 of ventricular band 122, entering from a terminal end of anterior band 136 or 138 and exiting from a terminal end of posterior band 140 or 142. Guide wire 198 is advanced through the submitral space below the mitral valve leaflets in the ventricular space, as will be discussed in further detail elsewhere herein, for positioning ventricular band 122 at the precise location of the mitral valve leaflet. Guide wire 198 may either be separable from ventricular band 122 by withdrawal from channel 123, or be stably attached to ventricular band 122, extending through channel 123.

Aspects of the invention relate to methods for replacing or repairing a mitral valve of a heart. FIG. 21A to 21L illustrate an example method of using a transcatheter approach to deliver and implant apparatus 100 on a mitral valve leaflet of a heart, arranged to extend across the commissures of the mitral valve.

Figures 21A, 21B, 21C:
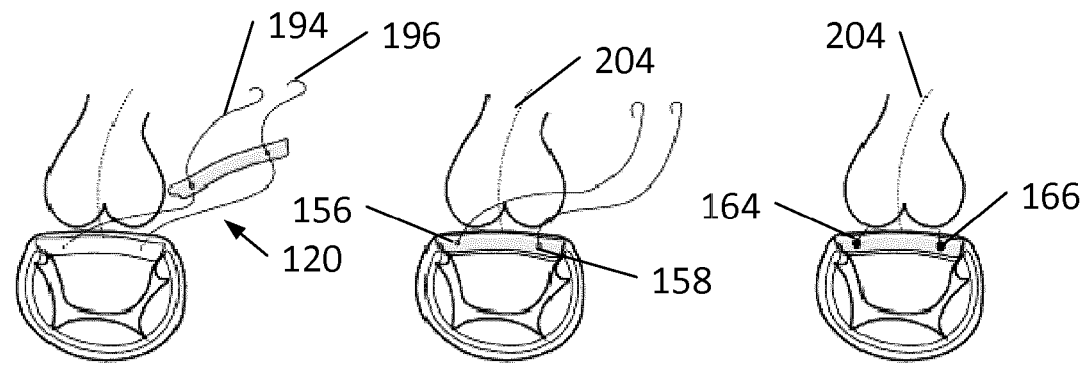

To implant apparatus 100, a guide wire 198 is inserted into a first access site of a subject and advanced using a transcatheter approach conventionally known. Referring to FIG. 21A, a catheter (not shown) is used to advance a distal end 220 of guide wire 198 intravascularly through the subject's femoral artery (not shown) and aortic valve 50 towards a ventricular surface of the anterior mitral valve leaflet 34 of a mitral valve 30, passing around the submitral space below the mitral valve leaflets 36, 38 in the ventricular space, and is snared to be exteriorized at the first access site. The opposing proximal end of guide wire 198 remains external to the subject, along with the exteriorized distal end 220. Ventricular band 122 (i.e., posterior band 134 and anterior band 132) is advanced along guide wire 198, within channel 123, through the femoral artery and aortic valve to loop around the mitral valve leaflets in the ventricular space. In the implanted configuration, posterior band 134 is positioned to encircle the submitral space below the mitral valve leaflets in the ventricular space; anterior band 132 is positioned on the ventricular side of the anterior mitral valve leaflet.

Figure 22:
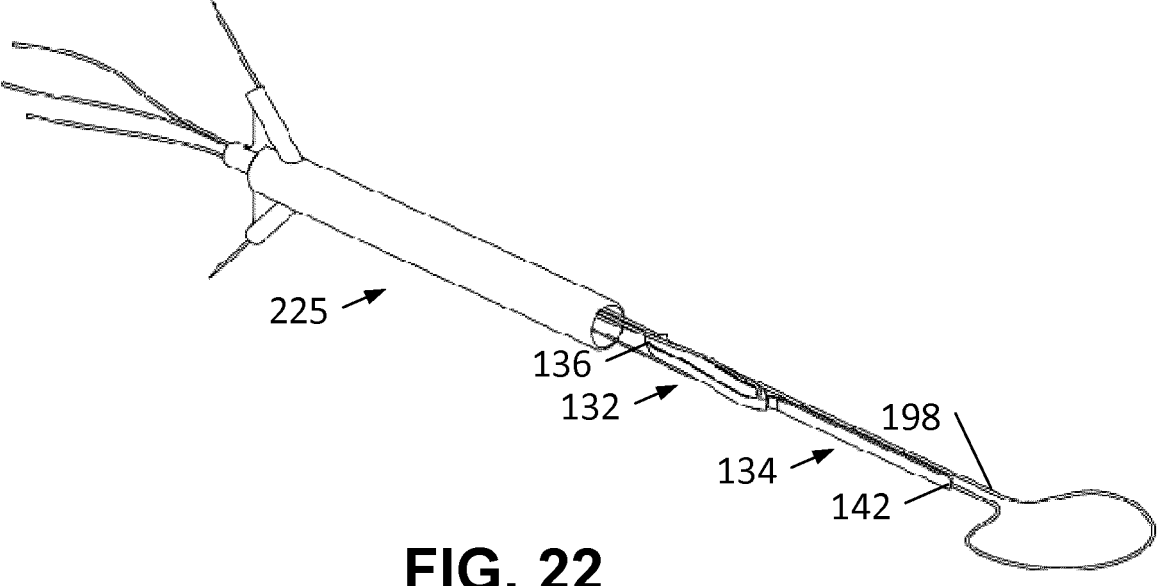
FIG. 22 is a side perspective view of a catheter advancing a ventricular band of the FIG. 4 apparatus, wherein the ventricular band is advanced in a linear configuration.

Ventricular band 122 may be advanced along guide wire 198 in a linear configuration. Referring to FIG. 22, in the linear configuration, anterior band 132 and posterior band 134, connected at one end and opened at the other opposing end, are arranged in one substantially straight and planar line, longitudinally extending from a terminal end 136 of anterior band 132 to a terminal end 142 of posterior band 134 along guide wire 198 supported by a catheter 225. In this configuration, ventricular band 122 may be advanced from under the mitral valve 30 (i.e., ventricular delivery).

Figure 23:
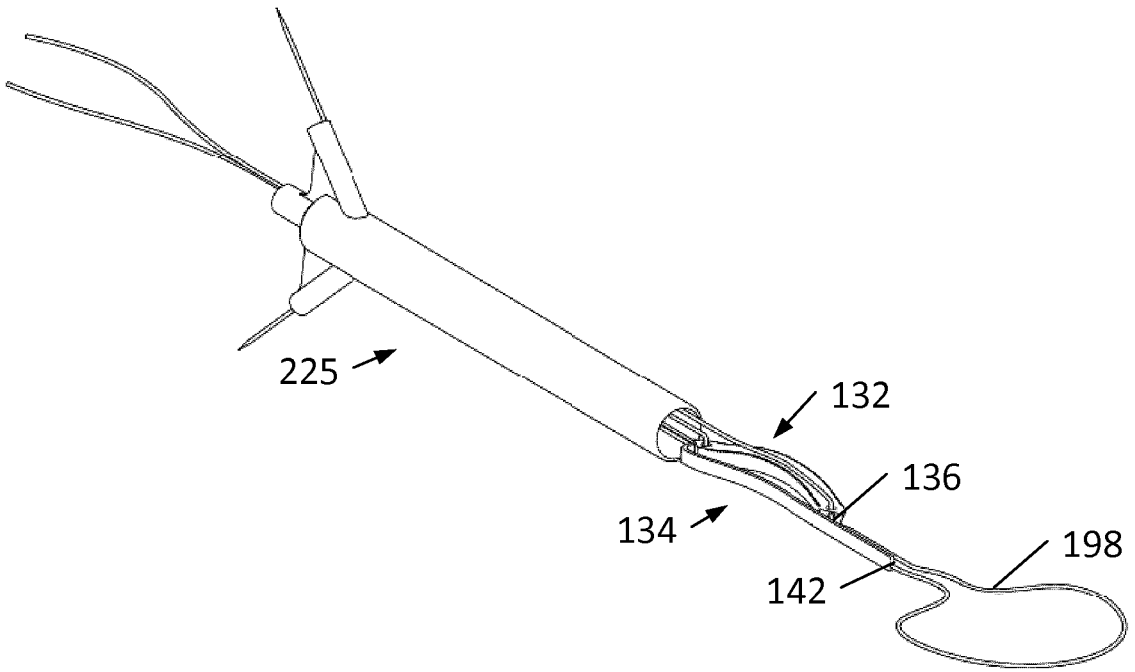
FIG. 23 is a side perspective view of a catheter advancing a ventricular band of the FIG. 4 apparatus, wherein the ventricular band is advanced in a bent configuration.

Ventricular band 122 may alternatively be advanced along guide wire 198 in a bent configuration. Referring to FIG. 23, in the bent configuration, anterior band 132 is folded towards posterior band 134 such that bands 132, 134 are arranged adjacent to each other along their longitudinal lengths on guide wire 198 supported by a catheter 225. In this configuration, ventricular band 122 may be advanced from over the top of the heart, from the left atrium through the mitral valve to reach the ventricular space (i.e., atrial delivery). An atrial delivery accommodates bulkier catheters.

Distal end 220 of guide wire 198 extends through channel 123 of ventricular band 122, entering into channel 126 of anterior band 132 and exiting from channel 222 of posterior band 134. In some embodiments, distal end 220 of guide wire 198 exits the subject's circulatory system without first connecting to anterior band 132 (FIG. 21B). In some embodiments, distal end 220 of guide wire 198 connects to anterior band 132 prior to exiting the subject's circulatory system (FIG. 21C). FIG. 8 illustrates an example means for connecting distal end 220 of guide wire 198 to anterior band 132. Closed loop 170 is arranged to extend from a terminal end 136 of anterior band 132. Distal end 220 of guide wire 198 is arranged to extend through closed loop 170 prior to exiting the subject's circulatory system. Guide wire 198 exits the subject's circulatory system through the same access site via the femoral artery as it enters.

Guide wires 194, 196, extending from the respective apertures 156, 158 of anterior band 132, pass through the anterior mitral valve leaflet, into the left atrium and are exteriorized therefrom through a catheter 226 (e.g., a transseptal catheter) across the atrial septum that originates at the femoral vein.

FIGS. 24A-24F and FIG. 25A-25F are example catheters 226 that can be used. Catheters 226 may be unifiable catheters. Catheter 226 has an elongated cylindrical body 230 extending longitudinally from a proximal end 232 to a curved distal portion 242, terminating in a distal end 234. Body 230 is defined by a main channel 231 extending longitudinally through the length of body 230. Main channel 231 may be divided into three separate channels, an afferent channel 238, and efferent channel 236 and a removable septum 240 arranged between afferent 238 and efferent 236 channels. Septum 240 is provided to allow snared guide wires to be drawn fully into and pulled through the main channel 231 of the body 230, to be exteriorized from an access site of a subject by removing septum 240 from body 230 after snaring.

Figures 24A, 24B, 24C, 24D, 24E, 24F:
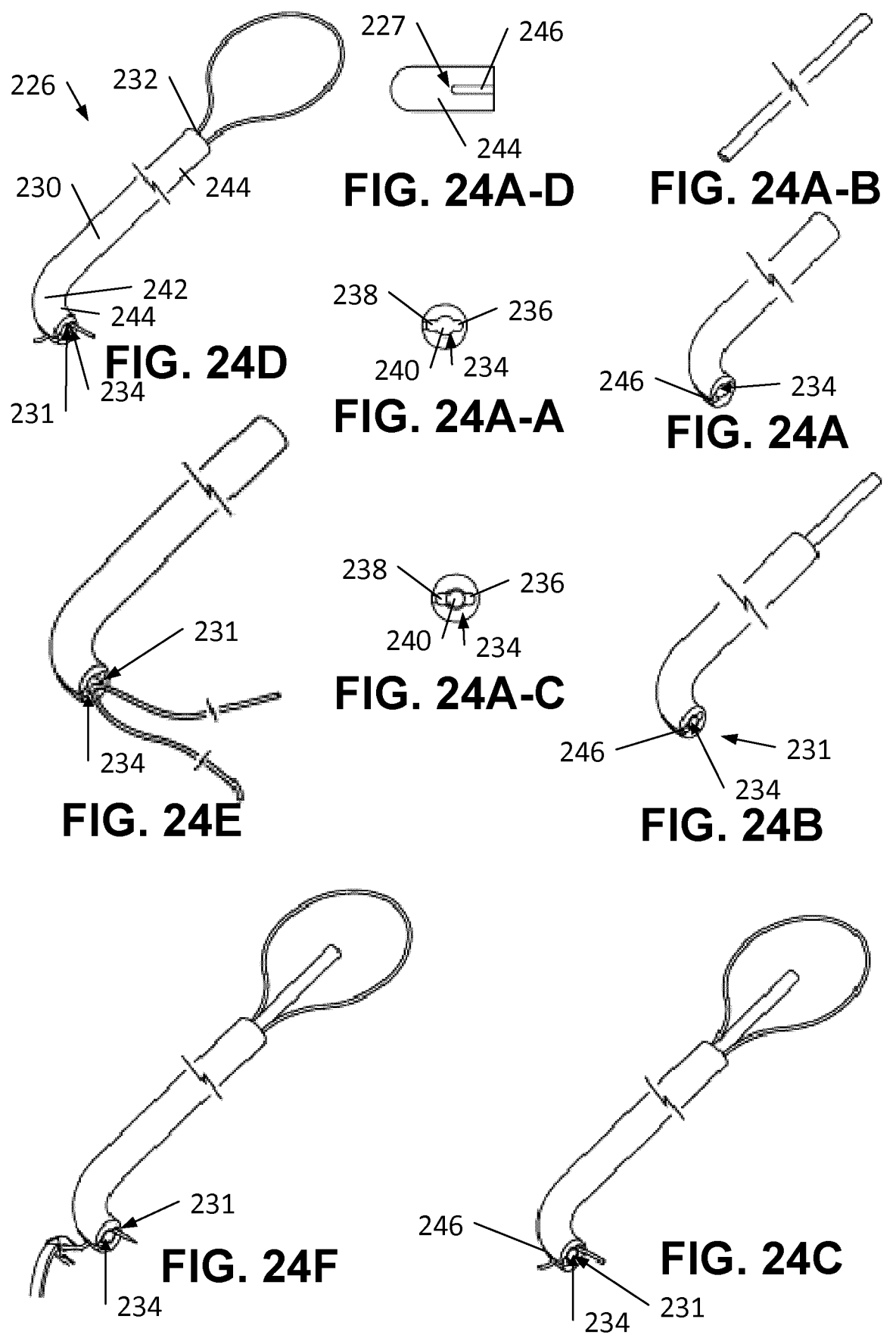

Catheter 226 is arranged to advance over each of guide wires 194, 196 sequentially for advancing guide wires 194, 196 through the anterior mitral valve leaflet 34. Referring to FIGS. 21E-21F, FIGS. 24A-24F and FIGS. 25A-25F, a catheter 226, having septum 240 being inserted within body 230, is first advanced over guide wire 196, through the afferent channel 238 of catheter 226, arranged to position distal end 234 of catheter 226 at the preferred leaflet puncture site. The proximal end of guide wire 196, which remains outside of the patient, is inserted into the efferent channel 236 of catheter 226 and advanced until the guide wire 196 perforates through the anterior mitral valve leaflet 36 at the desired location, thus entering the left atrium 20 (FIGS. 24C, 25C). A snare is then delivered to the atrium through the transseptal access (i.e., through the femoral vein, right atrium, across the septum and then the left atrium) where catheter 226 was previously placed to snare the formerly proximal end of guide wire 196 (not shown). The snare is withdrawn, and the septum 240 of catheter 226 is removed, unifying main channel 231 (i.e., by removing septum 240) (FIGS. 24D, 25D). The snare is withdrawn through the transseptal access. The snared guide wire 196 is then pulled through the unified catheter 226 from a terminal end 227 thereof to be exteriorized at the femoral vein (best seen in FIGS. 21G, FIGS. 24A-B and 25A-B). Particularly, guide wire 196, extending from anterior band 132, passes through the mitral valve leaflet into catheter 226 and exteriorized at the femoral vein.

Figure 26:
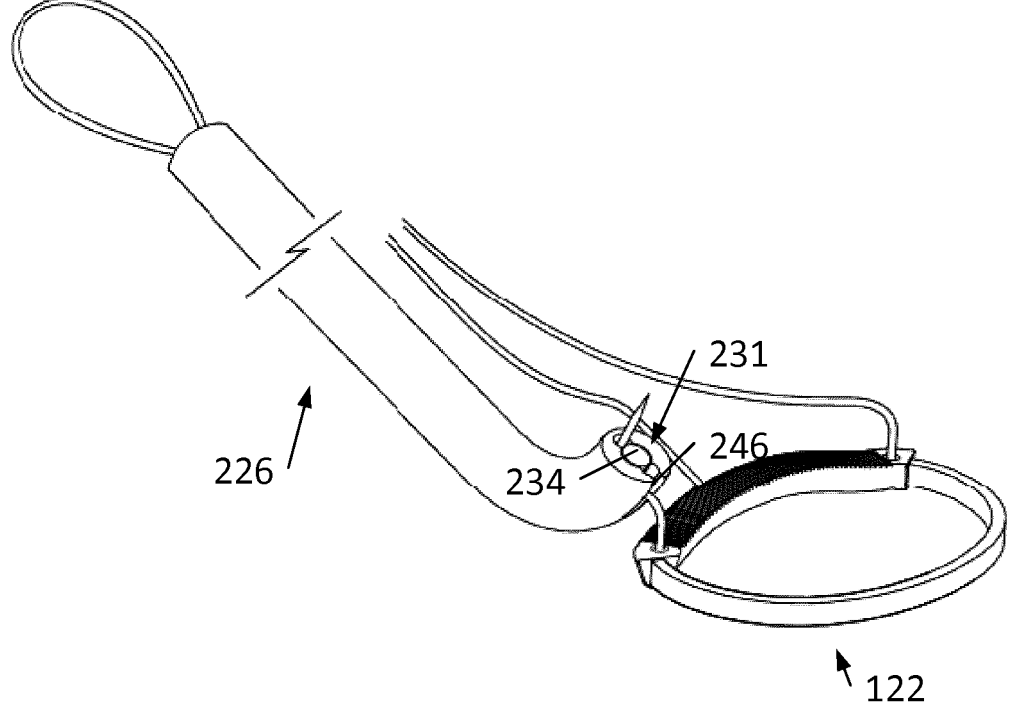
FIG. 26 is a top perspective view of a ventricular band of the FIG. 4 apparatus, showing a tethering guide wire, advanced by a catheter, engaging a guide wire extending from the anterior band of the ventricular band.

In some embodiments, terminal end 227 is at the distal end 234 of catheter 226 (as best seen in FIGS. 25A-A and 25A-B). Guide wires that extend through channels of these catheters extend substantially horizontally out of the catheter through openings 236, 238, substantially perpendicular to the surface of distal end 234. In some embodiments, terminal end 227 is at an end of a longitudinal slot 246, defined by an outer circumferential wall 244 at distal portion 242 of catheter 226, extending from one of afferent 238 or efferent 236 opening at distal end 234 of catheter 226 (as best seen in FIG. 24A-B). Guide wires that extend through channels of these catheters extend at an angle through the slot 246 (as best seen in FIG. 26).

Catheter 226 is then advanced over guide wire 194 to deliver guide wire 194 to the atrium through the mitral valve leaflet as was done with guide wire 196 (FIG. 21H), thus the steps will not be repeated here.

Central guide wire 204, extending from central aperture 200 or 202 of anterior band 132, passes through the left ventricle 40, aortic valve 50 and the aorta 60 and is exteriorized at the femoral artery (the first access site). Central guide wire 204 is later used to guide the incision of the mitral valve leaflet 34 from the left ventricle 40, after the attachment of atrial band 120 onto the anterior mitral valve leaflet 34 (as explained in the following paragraph). The proximal ends of guide wires 194, 196, 204 are all exteriorized at the femoral artery access site, remaining outside of the patient, while the opposing distal ends being attached to anterior band 132 during the initial delivery of atrial band 132 (FIGS. 21B-21E).

Figure 27:
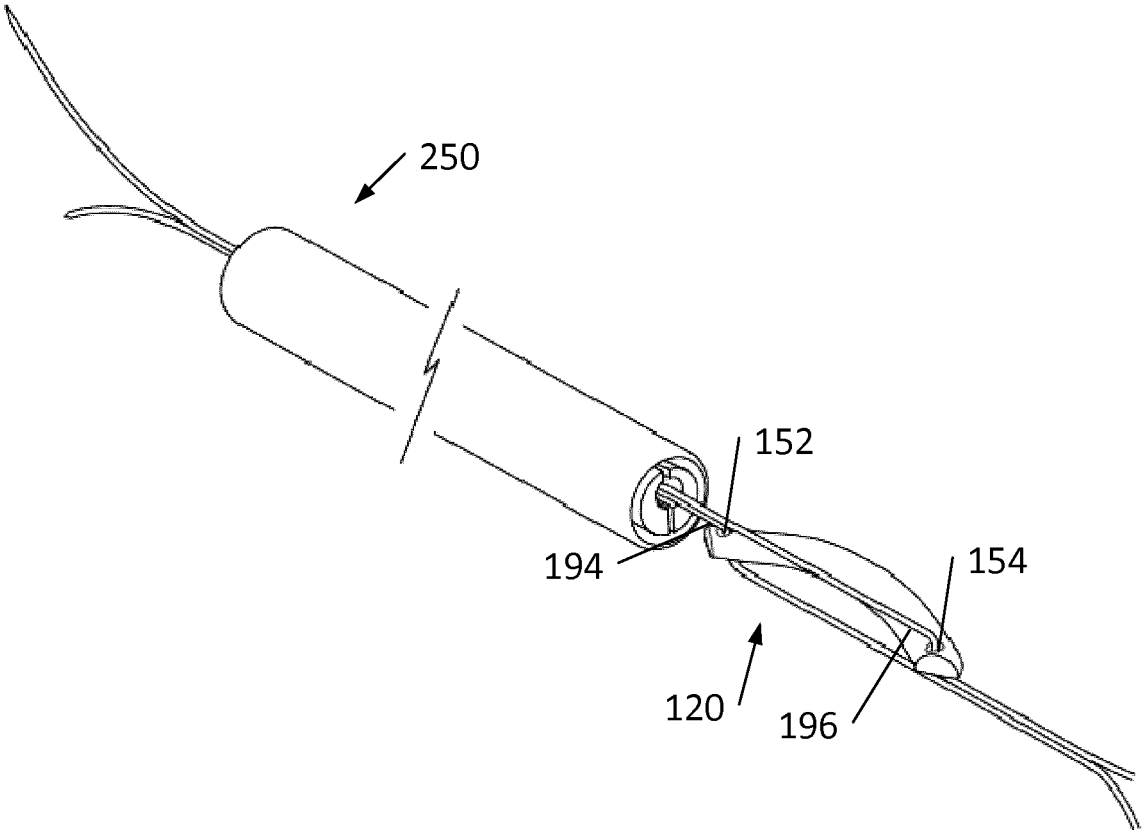
FIG. 27 is a side perspective view of a catheter advancing an atrial band of the FIG. 4 apparatus.

Snared guide wires 194, 196 pass through the left atrium 20 of the heart, cross the atrial septum, and are exteriorized on the venous side through the femoral vein. Snared guide wires 194, 196 are delivered to the atrial side to be used for delivery of atrial band 120 (FIG. 21I). Using catheter 250, atrial band 120 is advanced over guide wires 194, 196 through apertures 152, 154 to secure atrial band 120 to anterior band 132 for completing the implantation of apparatus 100 (catheter 250 is best shown in FIG. 27). Atrial band 120 passes through the femoral vein, right atrium and septum before being positioned on the atrial side of the anterior mitral valve leaflet 34 in the implanted configuration (FIG. 27). Locking members 164, 166 are advanced over the respective guide wires 194, 196 to secure atrial band 120 to anterior band 122 into position (as best seen in FIG. 21L). When apparatus 100 is secured into position, apparatus 100 extends across the commissures of the heart, with atrial band 120 and anterior band 132 arranged to press against the atrial and ventricular surfaces of the anterior mitral valve leaflets 34 respectively.

As illustrated in FIGS. 28A-28C and 29A-29C, a cutting device 248, guided by central guide wire 204, may be advanced towards the anterior mitral valve leaflet 34 of a subject's heart for precise cutting of leaflet 34. The cutting of anterior mitral valve leaflet 34 permits implantation of a TMVR prosthesis.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof; elements which are integrally formed may be considered to be connected or coupled;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An apparatus for clamping a mitral valve, the apparatus comprising:
   a ventricular band having an anterior band with a first terminal end and a second terminal end, the first and second terminal ends securable to the respective first and second terminal ends of a posterior band to form a closed ring;
   a pair of spaced-apart apertures defined by the anterior band positioned proximate to a respective first and second terminal ends thereof;
   an atrial band having an inner surface engageable with an inner surface of the anterior band, the atrial band defining a pair of spaced-apart apertures positioned proximate to a respective first and second terminal ends thereof for alignment with the pair of apertures defined by the anterior band;
   means for securing the atrial band to the anterior band; and
   means for securing the anterior band to the posterior band.

2. The apparatus according to claim 1 wherein the ventricular band and the atrial band are made of a flexibly deformable material, the ventricular and atrial bands are deformable between a natural state when the apparatus is in an unsecured configuration and a deformed state when the apparatus is in an implanted configuration.

3. The apparatus according to claim 2 wherein when the anterior and atrial bands are in the natural states, one or both of the inner surfaces of the anterior and atrial bands have a curvature with respect to the axial plane of the apparatus.

4. The apparatus according to claim 3, wherein when the anterior and atrial bands are in the natural states, one or both of the inner surfaces of the anterior and atrial bands have a U-shape configuration or an inverted U-shape configuration in the axial plane of the apparatus.

5. The apparatus according to claim 2 wherein when the anterior and atrial bands are in the natural states, one or both of the inner surfaces of the anterior and atrial bands are substantially planar in the axial plane of the apparatus.

6. The apparatus according to claim 2 wherein the inner surfaces of the anterior and atrial bands have the same shape or different shapes when the bands are in the natural states.

7. The apparatus according to claim 2 wherein when the anterior and atrial bands are in the deformed states, the inner surfaces of the anterior and atrial bands are deformed to assume a curvature or a substantially planar shape with respect to the axial plane of the apparatus.

8. The apparatus according to claim 1 wherein the atrial band and the anterior band are constructed from a material with equal stiffness or different stiffness.

9. The apparatus according to claim 1 wherein the atrial and anterior bands have an annular curvature in the natural and deformed states.

10. The apparatus according to claim 1 further comprises an attachment member extending from the atrial band at a portion proximate to the second terminal end thereof, the attachment member comprises a curve section extending from the portion to a straight section.

11. The apparatus according to claim 10 wherein the attachment member defines a channel extending through the straight and curved sections.

12. The apparatus according to claim 10 wherein the anterior band defines a channel extending from an opening defined by an upper surface of the anterior band proximate to the second terminal end of the anterior end to a closed end proximate to the first terminal end of the anterior band, the channel dimensioned to receive the straight section of the attachment member.

13. The apparatus according to claim 12 further comprising a guide wire extendable through the channel of the anterior band and the attachment member.

14. The apparatus according to claim 1 wherein the means for securing the atrial band to the anterior band comprises a pair of locking members each insertable into one of the apertures defined by the atrial and anterior bands.

15. The apparatus according to claim 1 wherein the means for securing the anterior band to the posterior band comprises a hook extending from the first terminal end of the posterior band, the hook connectable with a closed loop extending from the first terminal end of the anterior band.

16. The apparatus according to claim 1 wherein the means for securing the anterior band to the posterior band comprises a slot defined by the first terminal end of the anterior band, the slot dimensioned to snugly receive the first terminal end of the posterior band.

17. The apparatus according to claim 1 wherein the means for securing the anterior band to the posterior band comprises a connector having a pair of connecting members respectively insertable into a hole defined by each of the first terminal ends of the anterior and posterior bands.

18. The apparatus according to claim 1, wherein the posterior and anterior bands are constructed from a single continuous band, or from a plurality of modular units.

19. The apparatus according to claim 1, further comprising a central aperture defined by one or both of the atrial and anterior bands, wherein the central aperture is Positioned midway between the pair of spaced-apart apertures defined by the atrial and anterior bands, and wherein the apparatus further comprises a guide wire extending from the central aperture.

20. The apparatus according to claim 1 further comprising a channel extending through a length of the posterior band, and a guidewire extending through the channel of the posterior band.

\* \* \* \* \*